United States Patent
Smith et al.

(10) Patent No.: US 10,973,912 B2
(45) Date of Patent: Apr. 13, 2021

(54) TREATMENT FOR MYOPATHY

(71) Applicants: Children's Medical Center Corporation, Boston, MA (US); President and Fellows of Harvard College, Cambridge, MA (US)

(72) Inventors: Laura L. Smith, Boston, MA (US); Vandana Gupta, Lexington, MA (US); Alan Beggs, Needham, MA (US)

(73) Assignees: President and Fellows of Harvard College, Cambridge, MA (US); Children's Medical Center Corporation, Boston, MA (US)

(*) Notice: Subject to any disclaimer, the term of this patent is extended or adjusted under 35 U.S.C. 154(b) by 97 days.

(21) Appl. No.: 15/740,148

(22) PCT Filed: Jun. 29, 2016

(86) PCT No.: PCT/US2016/039998
§ 371 (c)(1),
(2) Date: Dec. 27, 2017

(87) PCT Pub. No.: WO2017/004142
PCT Pub. Date: Jan. 5, 2017

(65) Prior Publication Data
US 2018/0185478 A1 Jul. 5, 2018

Related U.S. Application Data

(60) Provisional application No. 62/185,760, filed on Jun. 29, 2015.

(51) Int. Cl.
| | | |
|---|---|---|
| A61K 39/395 | (2006.01) |
| A61K 31/713 | (2006.01) |
| A61K 31/137 | (2006.01) |
| A61K 31/165 | (2006.01) |
| A61K 31/192 | (2006.01) |
| A61K 31/216 | (2006.01) |
| A61K 31/345 | (2006.01) |
| A61K 31/409 | (2006.01) |
| A61K 31/4174 | (2006.01) |
| A61K 31/4365 | (2006.01) |
| A61K 31/4406 | (2006.01) |
| A61K 31/4422 | (2006.01) |
| A61K 31/517 | (2006.01) |
| A61K 31/635 | (2006.01) |
| A61K 31/135 | (2006.01) |
| A61P 43/00 | (2006.01) |
| A61P 21/00 | (2006.01) |

(52) U.S. Cl.
CPC ...... *A61K 39/39533* (2013.01); *A61K 31/135* (2013.01); *A61K 31/137* (2013.01); *A61K 31/165* (2013.01); *A61K 31/192* (2013.01); *A61K 31/216* (2013.01); *A61K 31/345* (2013.01); *A61K 31/409* (2013.01); *A61K 31/4174* (2013.01); *A61K 31/4365* (2013.01); *A61K 31/4406* (2013.01); *A61K 31/4422* (2013.01); *A61K 31/517* (2013.01); *A61K 31/635* (2013.01); *A61K 31/713* (2013.01); *A61P 21/00* (2018.01); *A61P 43/00* (2018.01); *A61K 2300/00* (2013.01)

(58) Field of Classification Search
None
See application file for complete search history.

(56) References Cited

U.S. PATENT DOCUMENTS

| | | |
|---|---|---|
| 3,306,820 A | 2/1967 | Krezanoski et al. |
| 6,218,428 B1 | 4/2001 | Chynn |
| 8,592,368 B2 | 11/2013 | Mohapatra |
| 2007/0117851 A1 | 5/2007 | Remenar et al. |
| 2010/0292306 A1 | 11/2010 | Carlson et al. |
| 2012/0321564 A1 | 12/2012 | Rowe |
| 2013/0164224 A1 | 6/2013 | Kim et al. |

FOREIGN PATENT DOCUMENTS

| | | |
|---|---|---|
| WO | WO 2008/030141 A1 | 3/2008 |
| WO | WO 2009/059425 A1 | 5/2009 |
| WO | WO 2014/117999 A1 | 8/2014 |

OTHER PUBLICATIONS

Drelicharz et al., NO and PGI(2) in coronary endothelial dysfunction in transgenic mice with dilated cardiomyopathy. Basic Res Cardiol. Sep. 2008;103(5):417-30. doi: 10.1007/s00395-008-0723-2. Epub Apr. 22, 2008.

Godbout et al., The effect of zimelidine, a serotonin-reuptake blocker, on cataplexy and daytime sleepiness of narcoleptic patients. Clin Neuropharmacol. 1986;9(1):46-51. Abstract Only.

Helenski et al., Platelet aggregation in feline cardiomyopathy. J Vet Intern Med. Jan.-Mar. 1987;1(1):24-8.

Kosugi et al., Changes of rabbit platelet function on simultaneous administration of ticlopidine hydrochloride and OKY-046. Int J Tissue React. 1991;13(3):123-9. Abstract Only.

Kröger et al., Metolazone in the treatment of advanced therapy-resistant dilated cardiomyopathy. Med Klin (Munich). Jun. 15, 1991;86(6):305-8, 332. German. Abstract Only.

Menazza et al., Oxidative stress by monoamine oxidases is causally involved in myofiber damage *in muscular dystrophy.* Hum Mol Genet. Nov. 1, 2010;19(21):4207-15. doi: 10.1093/hmg/ddq339. Epub Aug. 17, 2010.

(Continued)

*Primary Examiner* — John D Ulm
(74) *Attorney, Agent, or Firm* — Wolf, Greenfield & Sacks, P.C.

(57) ABSTRACT

Provided herein are methods and compositions for the treatment of myopathies.

13 Claims, 11 Drawing Sheets
Specification includes a Sequence Listing.

(56) References Cited

OTHER PUBLICATIONS

Nelson et al., Nifuroxazide inhibits survival of multiple myeloma cells by directly inhibiting STAT3. Blood. Dec. 15, 2008;112(13):5095-102. doi: 10.1182/blood-2007-12-129718. Epub Sep. 29, 2008.
Powers et al., Monoamine oxidase inhibition and furazolidone-induced cardiomyopathy in turkey poults. Poult Sci. Sep. 1983;62(9):1850-5. Abstract Only.
Price et al., Inhibition of JAK-STAT signaling stimulates adult satellite cell function. Nat Med. Oct. 2014;20(10):1174-81. doi: 10.1038/nm.3655. Epub Sep. 7, 2014. Erratum in: Nat Med. Apr. 2015;21(4):414. Nat Med. Oct. 2014;(10):1217.
Sabharwal, The link between stress disorders and autonomic dysfunction in muscular dystrophy. Front Physiol. Jan. 29, 2014;5:25. doi: 10.3389/fphys.2014.00025. eCollection 2014.
Sen et al., JAK kinase inhibition abrogates STAT3 activation and head and neck squamous cell carcinoma tumor growth. Neoplasia. Mar. 2015;17(3):256-64. doi: 10.1016/j.neo.2015.01.003.
Yu et al., Pargyline-induced myopathy with histochemical characteristics of Duchenne muscular dystrophy. Neurology. Mar. 1, 1974:24(3):237-244.
Zhou et al., Inhibition of PGI2 signaling by miconazole in vascular smooth muscle cells. Prostaglandins Other Lipid Mediat. Jul. 2006;80(1-2):28-34. Epub May 11, 2006.
[No Author Listed] Myopathy Information Page. National Institute of Neurological Disorders and Stroke. Accessed Apr. 30, 2020. https://www.ninds.nih.gov/disorders/all-disorders/myopathy-information-page. 4 pages.
Cardamone et al., Inherited Myopathies and Muscular Dystrophies. Semin Neurol 2008;28:250-259.

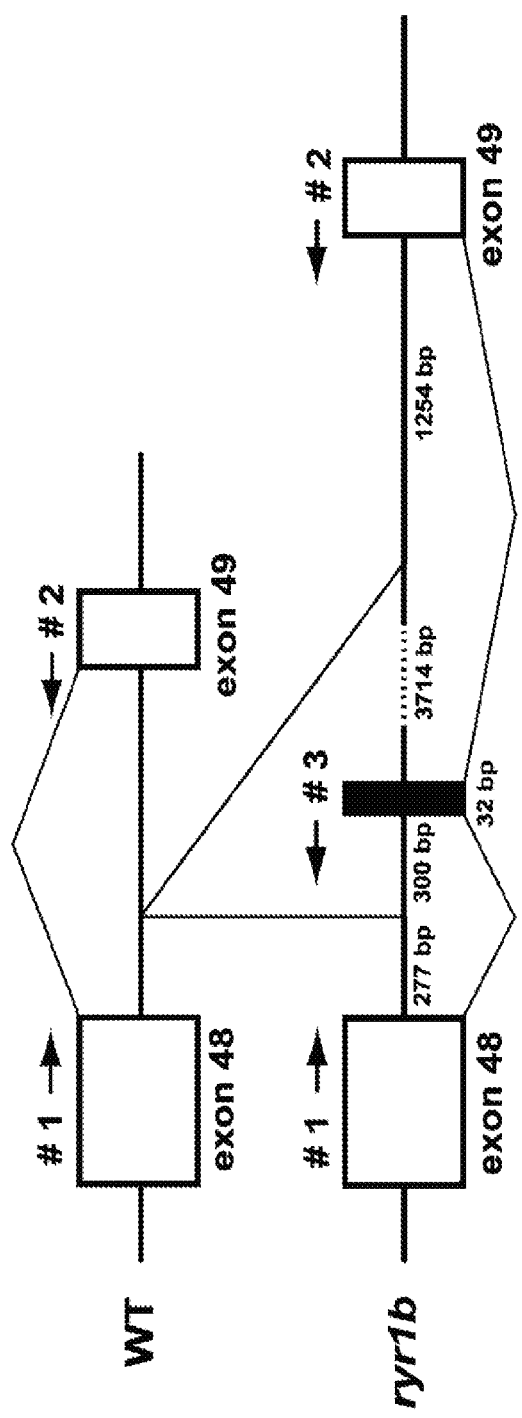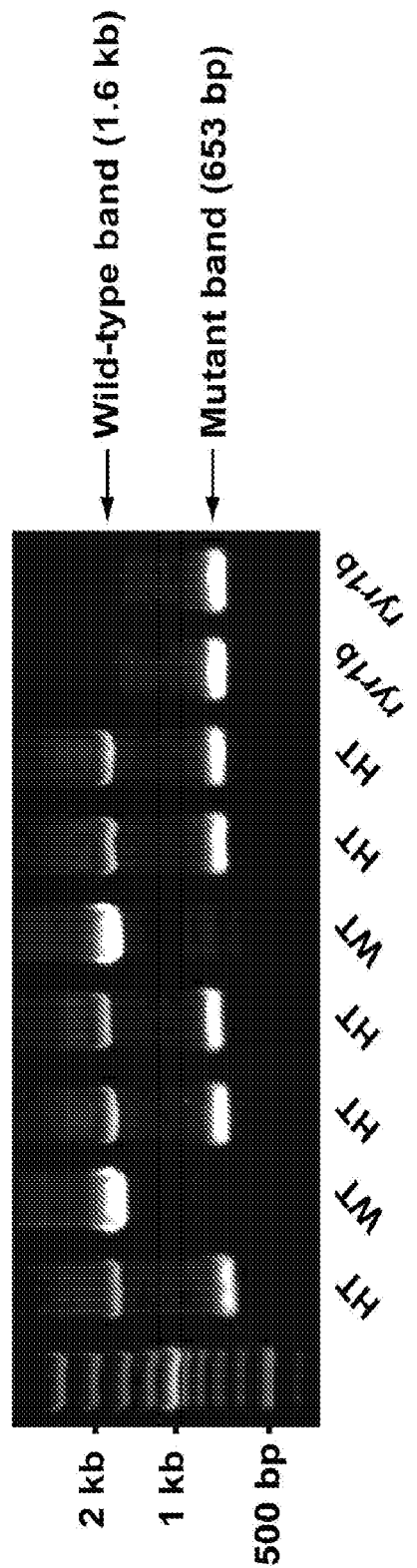
FIG. 3A
FIG. 3B

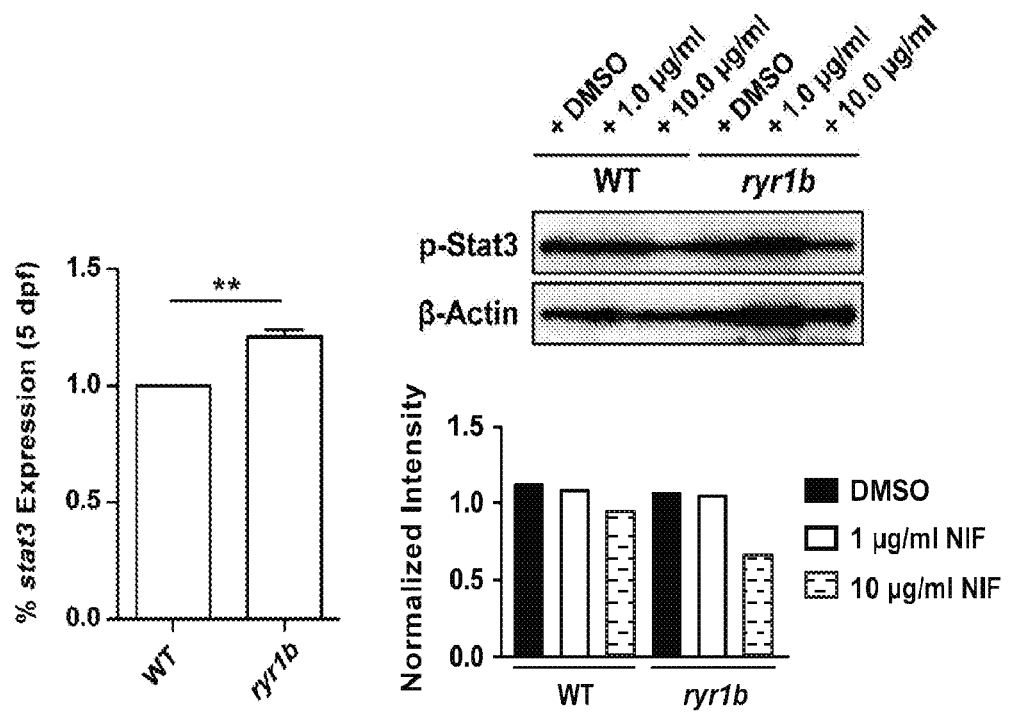
FIG. 8C          FIG. 8D
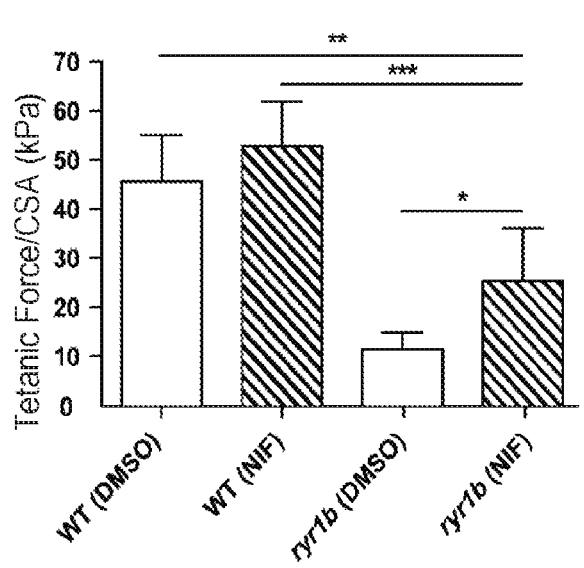    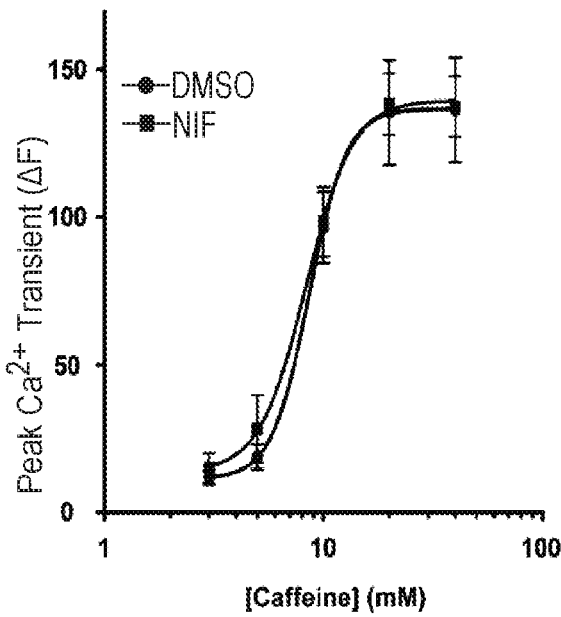
FIG. 9A          FIG. 9B Ketoprofen Nifuroxazide

SEQUENCE LISTING

```
<160> NUMBER OF SEQ ID NOS: 6

<210> SEQ ID NO 1
<211> LENGTH: 1132
<212> TYPE: PRT
<213> ORGANISM: Homo sapiens

<400> SEQUENCE: 1

Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
                100                 105                 110

Leu Tyr Arg Ile Arg Phe Tyr Phe Pro Arg Trp Tyr Cys Ser Gly Ser
```

-continued

```
            115                 120                 125
Asn Arg Ala Tyr Arg His Gly Ile Ser Arg Gly Ala Glu Ala Pro Leu
130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
                195                 200                 205

Phe Leu Pro Lys Cys Ile Arg Ala Lys Ile Gln Asp Tyr His Ile Leu
210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
            275                 280                 285

Ile Ile Thr Gly Asn Gly Gly Ile Gln Trp Ser Arg Gly Lys His Lys
290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
            355                 360                 365

Ile Asp Gly Tyr Tyr Arg Leu Thr Ala Asp Ala His His Tyr Leu Cys
370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
            435                 440                 445

Tyr Lys His Cys Leu Ile Thr Lys Asn Glu Asn Glu Tyr Asn Leu
            450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
                500                 505                 510

Arg Thr Asn Gly Val Ser Asp Val Pro Thr Ser Pro Thr Leu Gln Arg
            515                 520                 525

Pro Thr His Met Asn Gln Met Val Phe His Lys Ile Arg Asn Glu Asp
            530                 535                 540
```

```
Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
            565                 570                 575

Glu Val Leu Leu Lys Val Leu Asp Lys Ala His Arg Asn Tyr Ser Glu
                580                 585                 590

Ser Phe Phe Glu Ala Ala Ser Met Met Ser Lys Leu Ser His Lys His
            595                 600                 605

Leu Val Leu Asn Tyr Gly Val Cys Val Cys Gly Asp Glu Asn Ile Leu
610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
                660                 665                 670

Asn Val Cys Ala Lys Asn Ile Leu Leu Ile Arg Glu Asp Arg Lys
            675                 680                 685

Thr Gly Asn Pro Pro Phe Ile Lys Leu Ser Asp Pro Gly Ile Ser Ile
690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
                740                 745                 750

Pro Leu Ser Ala Leu Asp Ser Gln Arg Lys Leu Gln Phe Tyr Glu Asp
                755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
            835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
                900                 905                 910

Tyr Lys Gly Val Cys Tyr Ser Ala Gly Arg Arg Asn Leu Lys Leu Ile
            915                 920                 925

Met Glu Tyr Leu Pro Tyr Gly Ser Leu Arg Asp Tyr Leu Gln Lys His
            930                 935                 940

Lys Glu Arg Ile Asp His Ile Lys Leu Leu Gln Tyr Thr Ser Gln Ile
945                 950                 955                 960
```

```
Cys Lys Gly Met Glu Tyr Leu Gly Thr Lys Arg Tyr Ile His Arg Asp
                965                 970                 975
Leu Ala Thr Arg Asn Ile Leu Val Glu Asn Glu Asn Arg Val Lys Ile
            980                 985                 990
Gly Asp Phe Gly Leu Thr Lys Val Leu Pro Gln Asp Lys Glu Tyr Tyr
        995                 1000                1005
Lys Val Lys Glu Pro Gly Glu Ser Pro Ile Phe Trp Tyr Ala Pro
    1010                1015                1020
Glu Ser Leu Thr Glu Ser Lys Phe Ser Val Ala Ser Asp Val Trp
    1025                1030                1035
Ser Phe Gly Val Val Leu Tyr Glu Leu Phe Thr Tyr Ile Glu Lys
    1040                1045                1050
Ser Lys Ser Pro Pro Ala Glu Phe Met Arg Met Ile Gly Asn Asp
    1055                1060                1065
Lys Gln Gly Gln Met Ile Val Phe His Leu Ile Glu Leu Leu Lys
    1070                1075                1080
Asn Asn Gly Arg Leu Pro Arg Pro Asp Gly Cys Pro Asp Glu Ile
    1085                1090                1095
Tyr Met Ile Met Thr Glu Cys Trp Asn Asn Val Asn Gln Arg
    1100                1105                1110
Pro Ser Phe Arg Asp Leu Ala Leu Arg Val Asp Gln Ile Arg Asp
    1115                1120                1125
Asn Met Ala Gly
    1130

<210> SEQ ID NO 2
<211> LENGTH: 851
<212> TYPE: PRT
<213> ORGANISM: Homo sapiens

<400> SEQUENCE: 2

Met Ala Gln Trp Glu Met Leu Gln Asn Leu Asp Ser Pro Phe Gln Asp
1               5                   10                  15
Gln Leu His Gln Leu Tyr Ser His Ser Leu Leu Pro Val Asp Ile Arg
            20                  25                  30
Gln Tyr Leu Ala Val Trp Ile Glu Asp Gln Asn Trp Gln Glu Ala Ala
        35                  40                  45
Leu Gly Ser Asp Asp Ser Lys Ala Thr Met Leu Phe Phe His Phe Leu
    50                  55                  60
Asp Gln Leu Asn Tyr Glu Cys Gly Arg Cys Ser Gln Asp Pro Glu Ser
65                  70                  75                  80
Leu Leu Leu Gln His Asn Leu Arg Lys Phe Cys Arg Asp Ile Gln Pro
                85                  90                  95
Phe Ser Gln Asp Pro Thr Gln Leu Ala Glu Met Ile Phe Asn Leu Leu
            100                 105                 110
Leu Glu Glu Lys Arg Ile Leu Ile Gln Ala Gln Arg Ala Gln Leu Glu
        115                 120                 125
Gln Gly Glu Pro Val Leu Glu Thr Pro Val Glu Ser Gln Gln His Glu
    130                 135                 140
Ile Glu Ser Arg Ile Leu Asp Leu Arg Ala Met Met Glu Lys Leu Val
145                 150                 155                 160
Lys Ser Ile Ser Gln Leu Lys Asp Gln Gln Asp Val Phe Cys Phe Arg
                165                 170                 175
Tyr Lys Ile Gln Ala Lys Gly Lys Thr Pro Ser Leu Asp Pro His Gln
            180                 185                 190
```

```
Thr Lys Glu Gln Lys Ile Leu Gln Glu Thr Leu Asn Glu Leu Asp Lys
        195                 200                 205

Arg Arg Lys Glu Val Leu Asp Ala Ser Lys Ala Leu Leu Gly Arg Leu
    210                 215                 220

Thr Thr Leu Ile Glu Leu Leu Pro Lys Leu Glu Glu Trp Lys Ala
225                 230                 235                 240

Gln Gln Gln Lys Ala Cys Ile Arg Ala Pro Ile Asp His Gly Leu Glu
                245                 250                 255

Gln Leu Glu Thr Trp Phe Thr Ala Gly Ala Lys Leu Leu Phe His Leu
                260                 265                 270

Arg Gln Leu Leu Lys Glu Leu Lys Gly Leu Ser Cys Leu Val Ser Tyr
                275                 280                 285

Gln Asp Asp Pro Leu Thr Lys Gly Val Asp Leu Arg Asn Ala Gln Val
        290                 295                 300

Thr Glu Leu Leu Gln Arg Leu Leu His Arg Ala Phe Val Val Glu Thr
305                 310                 315                 320

Gln Pro Cys Met Pro Gln Thr Pro His Arg Pro Leu Ile Leu Lys Thr
                325                 330                 335

Gly Ser Lys Phe Thr Val Arg Thr Arg Leu Leu Val Arg Leu Gln Glu
                340                 345                 350

Gly Asn Glu Ser Leu Thr Val Glu Val Ser Ile Asp Arg Asn Pro Pro
                355                 360                 365

Gln Leu Gln Gly Phe Arg Lys Phe Asn Ile Leu Thr Ser Asn Gln Lys
        370                 375                 380

Thr Leu Thr Pro Glu Lys Gly Gln Ser Gln Gly Leu Ile Trp Asp Phe
385                 390                 395                 400

Gly Tyr Leu Thr Leu Val Glu Gln Arg Ser Gly Gly Ser Gly Lys Gly
                405                 410                 415

Ser Asn Lys Gly Pro Leu Gly Val Thr Glu Glu Leu His Ile Ile Ser
                420                 425                 430

Phe Thr Val Lys Tyr Thr Tyr Gln Gly Leu Lys Gln Glu Leu Lys Thr
                435                 440                 445

Asp Thr Leu Pro Val Val Ile Ile Ser Asn Met Asn Gln Leu Ser Ile
        450                 455                 460

Ala Trp Ala Ser Val Leu Trp Phe Asn Leu Leu Ser Pro Asn Leu Gln
465                 470                 475                 480

Asn Gln Gln Phe Phe Ser Asn Pro Pro Lys Ala Pro Trp Ser Leu Leu
                485                 490                 495

Gly Pro Ala Leu Ser Trp Gln Phe Ser Ser Tyr Val Gly Arg Gly Leu
                500                 505                 510

Asn Ser Asp Gln Leu Ser Met Leu Arg Asn Lys Leu Phe Gly Gln Asn
                515                 520                 525

Cys Arg Thr Glu Asp Pro Leu Leu Ser Trp Ala Asp Phe Thr Lys Arg
        530                 535                 540

Glu Ser Pro Pro Gly Lys Leu Pro Phe Trp Thr Trp Leu Asp Lys Ile
545                 550                 555                 560

Leu Glu Leu Val His Asp His Leu Lys Asp Leu Trp Asn Asp Gly Arg
                565                 570                 575

Ile Met Gly Phe Val Ser Arg Ser Gln Glu Arg Arg Leu Leu Lys Lys
                580                 585                 590

Thr Met Ser Gly Thr Phe Leu Leu Arg Phe Ser Glu Ser Ser Glu Gly
                595                 600                 605
```

Gly Ile Thr Cys Ser Trp Val Glu His Gln Asp Asp Lys Val Leu
    610                 615                 620

Ile Tyr Ser Val Gln Pro Tyr Thr Lys Glu Val Leu Gln Ser Leu Pro
625                 630                 635                 640

Leu Thr Glu Ile Ile Arg His Tyr Gln Leu Leu Thr Glu Glu Asn Ile
                645                 650                 655

Pro Glu Asn Pro Leu Arg Phe Leu Tyr Pro Arg Ile Pro Arg Asp Glu
            660                 665                 670

Ala Phe Gly Cys Tyr Tyr Gln Glu Lys Val Asn Leu Gln Glu Arg Arg
        675                 680                 685

Lys Tyr Leu Lys His Arg Leu Ile Val Val Ser Asn Arg Gln Val Asp
    690                 695                 700

Glu Leu Gln Gln Pro Leu Glu Leu Lys Pro Glu Pro Glu Leu Glu Ser
705                 710                 715                 720

Leu Glu Leu Glu Leu Gly Leu Val Pro Glu Pro Glu Leu Ser Leu Asp
                725                 730                 735

Leu Glu Pro Leu Leu Lys Ala Gly Leu Asp Leu Gly Pro Glu Leu Glu
            740                 745                 750

Ser Val Leu Glu Ser Thr Leu Glu Pro Val Ile Glu Pro Thr Leu Cys
        755                 760                 765

Met Val Ser Gln Thr Val Pro Glu Pro Asp Gln Gly Pro Val Ser Gln
    770                 775                 780

Pro Val Pro Glu Pro Asp Leu Pro Cys Asp Leu Arg His Leu Asn Thr
785                 790                 795                 800

Glu Pro Met Glu Ile Phe Arg Asn Cys Val Lys Ile Glu Glu Ile Met
                805                 810                 815

Pro Asn Gly Asp Pro Leu Leu Ala Gly Gln Asn Thr Val Asp Glu Val
            820                 825                 830

Tyr Val Ser Arg Pro Ser His Phe Tyr Thr Asp Gly Pro Leu Met Pro
        835                 840                 845

Ser Asp Phe
    850

<210> SEQ ID NO 3
<211> LENGTH: 770
<212> TYPE: PRT
<213> ORGANISM: Homo sapiens

<400> SEQUENCE: 3

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
            130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
530                 535                 540

```
Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
            565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
        610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
            675                 680                 685

Pro Glu Ser Gln Glu His Pro Glu Ala Asp Pro Gly Ser Ala Ala Pro
            690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
            755                 760                 765

Pro Met
    770

<210> SEQ ID NO 4
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 4
gtgggtttct tgcccgatat gagagcttca                                      30

<210> SEQ ID NO 5
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 5
aacagtgggg cacatttagt gagcagagg                                       29

<210> SEQ ID NO 6
<211> LENGTH: 32
<212> TYPE: DNA
<213> ORGANISM: Artificial Sequence
<220> FEATURE:
<223> OTHER INFORMATION: Synthetic Polynucleotide
```

```
<400> SEQUENCE: 6
ctttaaataa gctctgtggc attggttgac tc                                         32
```

US 10,973,912 B2

TREATMENT FOR MYOPATHY

RELATED APPLICATIONS

This application is a national stage filing under 35 U.S.C. 371 of International Application PCT/US2016/039998, filed Jun. 29, 2016, which claims the benefit under 35 U.S.C. § 119(e) of U.S. Provisional Patent Application filed Jun. 29, 2015, entitled "TREATMENT FOR MYOPATHY", Ser. No. 62/185,760, the contents of which are incorporated by reference herein in their entirety. International Application PCT/US2016/039998 was published under PCT Article 21(2) in English.

GOVERNMENT SUPPORT

This invention was made with government support under grants R01AR044345, F31NS081928, and K01AR062601 awarded by the National Institutes of Health. The government has certain rights in the invention.

BACKGROUND OF INVENTION

Myopathies are a heterogeneous group of disorders that manifest as skeletal muscle weakness and are defined by the presence of morphological features on muscle biopsy. Treatment for myopathies has traditionally been limited to supportive and palliative care. There remains a need for effective and specific treatments for myopathies.

SUMMARY OF THE INVENTION

The disclosure is based, in part, on a throughput chemical screen on the relatively relaxed (ryr1b) zebrafish that identified inhibitors of Janus kinase-Signal Transducer and Activator of Transcription (JAK-STAT) pathway. JAK-STAT cytokine signaling was identified as a druggable molecular pathway to treat the manifestations of myopathies.

In some aspects, the disclosure provides a method of treating a myopathy, the method comprising administering to a subject having a myopathy an effective amount of an inhibitor of Janus kinase-Signal Transducer and Activator of Transcription (JAK-STAT) pathway.

In some embodiments, the inhibitor of JAK-STAT is a small molecule, an antisense oligonucleotide, a small interfering RNA (siRNA), or an antibody. In some embodiments, the inhibitor of JAK-STAT is selected from the group consisting of: nifuroxazide, ketoprofen, sulfasalazine, 5,15-diphenylporphyrin, and AG490.

In some embodiments, the inhibitor of JAK-STAT is an inhibitor of JAK. In some embodiments, the inhibitor of JAK-STAT is an inhibitor of STAT. In some embodiments, the inhibitor of JAK-STAT is an inhibitor of STAT3.

Other aspects of the disclosure relate to a method of treating a myopathy, the method comprising administering to a subject having a myopathy an effective amount of an agent selected from the group consisting of: nifuroxazide, ketoprofen, sulfasalazine, 5,15-diphenylporphyrin, pargyline hydrochloride, metolazone, zimelidine dihydrochloride monohydrate, miconazole, ticlopidine hydrochloride, iohexol, benoxinate hydrochloride, nimodipine, tranylcypromine hydrochloride, and AG490.

In some embodiments, the myopathy is congenital, myofibrillar, endocrine or metabolic, toxic, or caused by a systemic illness. In some embodiments, the congenital myopathy is a ryanodine receptor 1 (RYR1)-related myopathy. In some embodiments, the congenital myopathy is selected from the group consisting of: central core disease (CCD), multiminicore disease (MmD), centronuclear myopathy (CNM), nemaline myopathy (NM), core-rod myopathy, and congenital fiber-type disproportion (CFTD). In some embodiments, RYR1-related myopathy is selected from the group consisting of: central core disease (CCD), multiminicore disease (MmD), centronuclear myopathy (CNM), nemaline myopathy (NM), core-rod myopathy, and congenital fiber-type disproportion (CFTD).

Other aspects of the disclosure relate to an inhibitor of Janus kinase-Signal Transducer and Activator of Transcription (JAK-STAT) pathway for use in the treatment of a myopathy.

In some embodiments, the inhibitor of JAK-STAT is a small molecule, an antisense oligonucleotide, a small interfering RNA (siRNA), or an antibody. In some embodiments, the inhibitor of JAK-STAT is selected from the group consisting of: nifuroxazide, ketoprofen, sulfasalazine, 5,15-diphenylporphyrin, and AG490. In some embodiments, the inhibitor of JAK-STAT is an inhibitor of JAK. In some embodiments, the inhibitor of JAK-STAT is an inhibitor of STAT. In some embodiments, the inhibitor of JAK-STAT is an inhibitor of STAT3.

Other aspects of the disclosure relate to an agent for use in the treatment of a myopathy, wherein the agent is selected from the group consisting of: nifuroxazide, ketoprofen, sulfasalazine, 5,15-diphenylporphyrin, pargyline hydrochloride, metolazone, zimelidine dihydrochloride monohydrate, miconazole, ticlopidine hydrochloride, iohexol, benoxinate hydrochloride, nimodipine, tranylcypromine hydrochloride, and AG490.

In some embodiments the myopathy is congenital, myofibrillar, endocrine or metabolic, toxic, or caused by a systemic illness. In some embodiments, the congenital myopathy is a ryanodine receptor 1 (RYR1)-related myopathy.

In some embodiments, the congenital myopathy is selected from the group consisting of: central core disease (CCD), multiminicore disease (MmD), centronuclear myopathy (CNM), nemaline myopathy (NM), core-rod myopathy, and congenital fiber-type disproportion (CFTD).

In some embodiments, RYR1-related myopathy is selected from the group consisting of: central core disease (CCD), multiminicore disease (MmD), centronuclear myopathy (CNM), nemaline myopathy (NM), core-rod myopathy, and congenital fiber-type disproportion (CFTD).

Yet other aspects of the disclosure relate to the use of an inhibitor of Janus kinase-Signal Transducer and Activator of Transcription (JAK-STAT) in the manufacture of a medicament for the treatment of a myopathy.

In some embodiments, the inhibitor of JAK-STAT is a small molecule, an antisense oligonucleotide, a small interfering RNA (siRNA), or an antibody. In some embodiments, the inhibitor of JAK-STAT is selected from the group consisting of: nifuroxazide, ketoprofen, sulfasalazine, 5,15-diphenylporphyrin, and AG490. In some embodiments, the inhibitor of JAK-STAT is an inhibitor of JAK. In some embodiments, the inhibitor of JAK-STAT is an inhibitor of STAT. In some embodiments, the inhibitor of JAK-STAT is an inhibitor of STAT3.

Still other aspects of the disclosure relate to the use of an agent in the manufacture of a medicament for the treatment of a myopathy, wherein the agent is selected from the group consisting of: nifuroxazide, ketoprofen, sulfasalazine, 5,15-diphenylporphyrin, pargyline hydrochloride, metolazone, zimelidine dihydrochloride monohydrate, miconazole, ticlopidine hydrochloride, iohexol, benoxinate hydrochloride, nimodipine, tranylcypromine hydrochloride, and AG490.

In some embodiments the myopathy is congenital, myofibrillar, endocrine or metabolic, toxic, or caused by a systemic illness. In some embodiments, the congenital myopathy is a ryanodine receptor 1 (RYR1)-related myopathy.

In some embodiments, the congenital myopathy is selected from the group consisting of: central core disease (CCD), multiminicore disease (MmD), centronuclear myopathy (CNM), nemaline myopathy (NM), core-rod myopathy, and congenital fiber-type disproportion (CFTD).

In some embodiments, RYR1-related myopathy is selected from the group consisting of: central core disease (CCD), multiminicore disease (MmD), centronuclear myopathy (CNM), nemaline myopathy (NM), core-rod myopathy, and congenital fiber-type disproportion (CFTD).

These and other aspects of the disclosure, as well as various advantages and utilities will be apparent with reference to the Detailed Description of the Invention. Each aspect of the disclosure can encompass various embodiments as will be understood.

All documents identified in this application are incorporated in their entirety herein by reference.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. The patent or application file contains at least one drawing executed in color, Copies of this patent or patent application publication with color drawing(s) will be provided by the Office upon request and payment of the necessary fee.

In FIG. 2A, four days following treatment with DMSO or drug, all larvae present in each screened well were counted and evaluated in terms of mobility using a touch-evoked escape behavior assay. Behaviors were scored using the following numeric scoring system: 3=4-6 cm, fast (wild-type); 2=2-4 cm (moderate); 1=<2 cm, slow (ryr1b); 0=no movement (dead). A representative response of each score is shown. FIG. 2B shows the average swimming distance of 5 days post-fertilization (dpf) larvae in response to touch (WT/HT: 6.2±0.8 cm/0.1 s; ryr1b: 0.5±0.3 cm/0.1 s). Motor functions were quantified using 15 embryos per group from three independent clutches. Significance was determined by a Student's t-test, $P=1.2\times10^{-25}$.

FIGS. 3A-3B show the genotyping of ryr1b larvae. In FIG. 3A, the ryr1b mutant allele carries a 4046 bp DNA insertion in the intron between exons 48 and 49 that includes an additional 32 bp sequence found in mutant cDNA. Schematic image adapted from Hirata et al. (2007) *Development*, 134: 2771-81. Genotypes of individual embryos were examined using three-primer genomic PCR. Primer binding sites are indicated. FIG. 3B is a representative agarose gel used for PCR-based genotyping of individual wild-type, heterozygous, and ryr1b mutant larvae.

FIGS. 8A-8D demonstrate that nifuroxazide acts on the ryr1b phenotype in a dose-dependent manner. FIG. 8A shows the dose-response for nifuroxazide (NIF). In two independent experiments, two pools of 20 larvae from heterozygous ryr1b matings were treated with DMSO or with one of three different concentrations of NIF (1.0-100.0 µg/mL) at 1 dpf and evaluated in terms of touch-evoked escape behaviors at 5 dpf (n=40). Following phenotypic scoring, all living embryos were genotyped using three-primer genomic PCR. Swimming scores for larvae genotype-confirmed as ryr1b homozygous mutants are shown as a percentage of the total number of living larvae in each dose category: 1=poor swimming; 2 or 3=moderate or wild-type swimming. NIF improved mobility of ryr1b mutants at a dose of 10 µg/mL. FIG. 8B shows the dose-response for 5,15-DPP, a known inhibitor of STAT3. 5,15-DPP improved mobility of select ryr1b mutants at a dose of 100 µg/mL, but also showed evidence of toxicity since treated pools consistently contained less than 25% genotyped ryr1b larvae.

FIG. 8C shows that zebrafish stat3 expression is significantly increased in ryr1b mutants compared to unaffected larvae from the same clutch at 5 dpf (P<0.005). FIG. 8D is a Western blot at 5 dpf showing levels of phosphorylated Stat3 in zebrafish suggesting that ryr1b mutations may increase Stat3 sensitivity to pharmacological inhibition. Phospho-Stat3 band intensities were normalized to β-Actin control bands and quantified in Image J (NIH).

FIGS. 9A-9B show that nifuroxazide increases the contractile strength of ryr1b skeletal muscles. In FIG. 9A, DMSO-treated ryr1b mutants exhibit reduced tetanic force per cross-sectional area (CSA) compared to DMSO-treated wild-type larvae at 5 dpf. Tetanic forces in mutants treated with NIF, however, are restored to wild-type levels at 5 dpf. Tetanic forces were measured following stimulation with 9 biphasic, 200 μs square-wave pulses at 300 Hz (WT-DMSO: 45.6±4.2 kPa, n=5; WT-NIF: 52.8±4.1 kPa, n=5; ryr1b-DMSO: 11.4±1.3 kPa, n=7; ryr1b-NIF: 25.4±4.0 kPa, n=7). Significance was determined by a one-way ANOVA (F=29.61, P<0.0001), followed by pairwise Tukey's HSD post hoc tests. FIG. 9B shows the dose response relationship between caffeine concentration and depolarization-induced calcium release in wild-type mouse myotubes. Prior to testing, myotubes were differentiated in either DMSO or NIF (20 μM) for 5 consecutive days (DMSO $EC_{50}$: 8.6 mM; NIF $EC_{50}$: 7.9 mM). Non-linear regression data of curves were not statistically different, as determined by an extra sum-of-squares F test (P=1.0).

In FIG. 10A, body angles of ryr1b mutants after 20 days of NIF treatment (10.0 μg/mL) are corrected and statistically indistinguishable from wild-type controls. FIG. 10B shows the quantification of body angle measurements. Angles were measured by first drawing/extending straight lines between the eyes of the larva as well as along the midline of the trunk (shown by dotted red lines). The angle of intersection was determined using Adobe Photoshop CS3 software (WT-DMSO: 179.1±0.9°, n=6; WT-NIF: 176.8±1.1°, n=6; ryr1b-DMSO: 142.6±6.2°, n=11; ryr1b-NIF: 174.4±2.0°, n=4). Significance was determined by a one-way ANOVA (F=13.60, P<0.0001), followed by pairwise Tukey's HSD post hoc tests. FIG. 10C shows the swimming behaviors of 20 dpf larvae quantified in terms of distance traveled during a 2.0-hour period using the Noldus Daniovision, a high-resolution system that allows for automated analysis of larval locations and orientations. Three independent trials were performed with larvae from three different clutches, examining a total of 14-20 wild-type and ryr1b larvae from both DMSO- and NIF-treated groups. Genotypes of individual embryos were confirmed by genomic PCR following the study. Significance was determined by a one-way ANOVA (F=10.03, P=0.0009), followed by pairwise Tukey's HSD post hoc tests. FIG. 10D shows monitored activities of DMSO- and NIF-treated wild-type and ryr1b zebrafish at 20 dpf using the Noldus Daniovision's infrared light source. One representative 20-minute time interval within the recording period is shown.

FIG. 12A depicts the chemical structures of ketoprofen and nifuroxazide. FIG. 12B is a dose-response graph for ketoprofen (KETO). Two pools of 20 larvae from heterozygous ryr1b matings were treated with DMSO or four different concentrations of KETO (1.0-100.0 μg/mL) at 1 dpf and evaluated in terms of touch-evoked escape behaviors at 5 dpf (n=40). Following phenotypic scoring, all living embryos were genotyped using three-primer genomic PCR. Swimming scores for larvae genotype-confirmed as ryr1b homozygous mutants are shown as a percentage of the total number of living larvae in each dose category: 1=poor swimming, 2 or 3=moderate or wild-type swimming. FIG. 12C shows a potential mechanistic link between candidate compounds via the IL-6/JAK2/STAT3 signaling pathway. Phosphorylated STATs form dimers, translocate to nuclei, and from there are associated with various transcriptional activities. Dubowitz, V. and Sewry, C. (2006) Muscle Biopsy: A Practical Approach. Elsevier-Health Sciences Division.

DETAILED DESCRIPTION OF THE INVENTION

Figure 1:
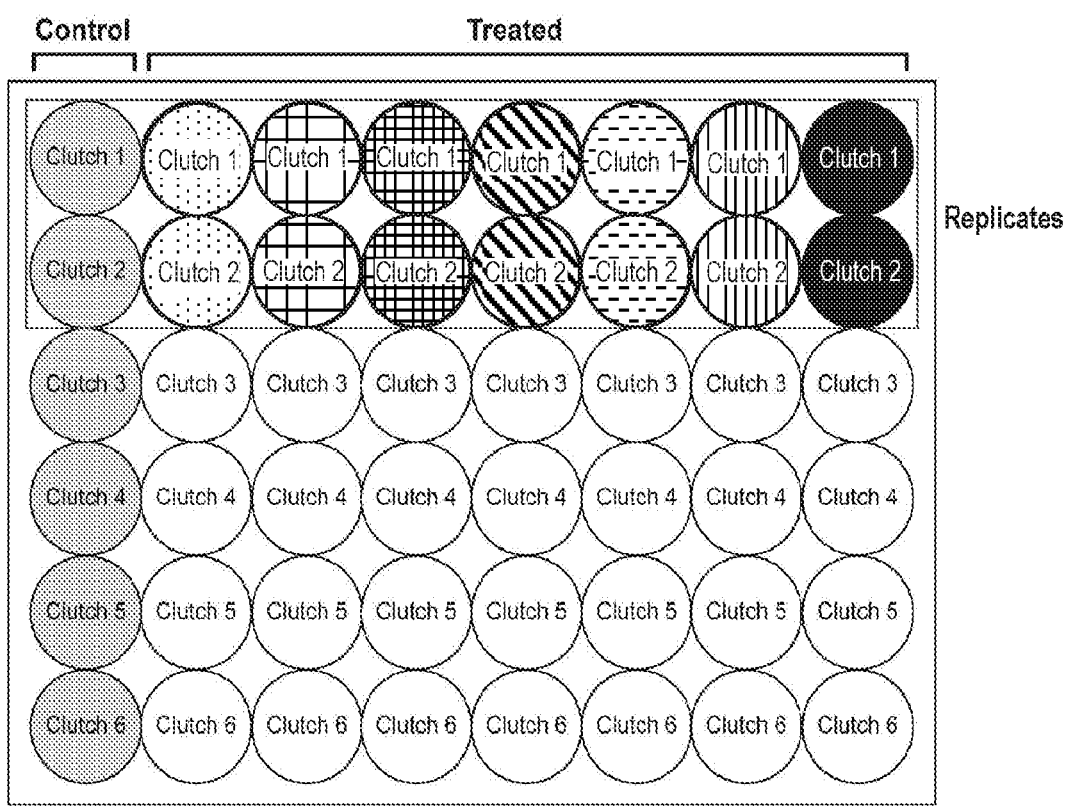
FIG. 1 is a representative diagram of a 48-well plate used in the ryr1b primary screen showing the chemical screening plate set-up. No two rows of the plate were filled with embryos from the same clutch, and each row contained a negative control well treated with vehicle only (0.4% DMSO). Experimental replicates were placed vertically from one another. An example treatment of the first two rows is illustrated, with negative controls in the first column shown in gray and replicate wells treated with the same chemical pool shown using different colors.

Aspects of the disclosure relate to methods for treating a myopathy. In some aspects, the disclosure is based, in part, on a two-tiered chemical screen aimed at identifying lead FDA-approved compounds that can rescue the function of skeletal muscle in the relatively relaxed zebrafish model of ryr1b mutation. In the primary screen, pools of four chemicals from the Prestwick2 chemical library (280 pools, 1120 chemicals) were scored for their ability to improve survival and postnatal motility of ryr1b homozygous mutant fry. Individual chemicals from hit pools were further evaluated in a secondary screen, and 12 candidate compounds were identified that could ameliorate the relatively relaxed muscle phenotype. One chemical, nifuroxazide, which is known to inhibit JAK-STAT cytokine signaling, restores the locomotive activities and corrects mild morphological abnormalities observed in ryr1b mutants.

Methods of Treatment

Aspects of the disclosure relate to a method of treating a myopathy. In some embodiments, the method comprises administering to a subject (e.g., a subject having a myopathy) an effective amount of an inhibitor of JAK-STAT pathway. Examples of an inhibitor of JAK-STAT pathway include but are not limited to: nifuroxazide, ketoprofen, sulfasalazine, 5,15-diphenylporphyrin, and AG490. Other examples of inhibitors of JAK-STAT pathway include: S31-201, fludarabine, stattic, niclosamide, SG-4-54, HO-3867, cryptotanshinone, cucurbitacin I, OPB-31121, resveratrol, pimozide, MS 1020, LLL12, ruxolitinib, tofacitinib, baricitinib, CYT387, filgotinib, GSK2586184, lestaurtinib, pacritinib, SB1518, SAR302503, XL019, AZD1480, INCB028050, INCB16562, tasocitinib, NVP-BSK805, TG101348, galiellactone, and CP-690550.

In some embodiments, the inhibitor of JAK-STAT pathway is an inhibitor of JAK. The inhibitor of JAK may be any inhibitor of JAK known in the art or as described herein. Examples of inhibitors of JAK include, but are not limited to: ruxolitinib, tofacitinib, baricitinib, CYT387, filgotinib, GSK2586184, lestaurtinib, pacritinib, SB1518, SAR302503, XL019, AZD1480, INCB028050, INCB16562, tasocitinib, NVP-BSK805, and TG101348

In some embodiments, the inhibitor of JAK-STAT pathway is an inhibitor of STAT. The inhibitor of STAT may be any inhibitor of STAT known in the art or as described herein. Examples of inhibitors of STAT include, but are not limited to: S31-201, fludarabine, stattic, niclosamide, nifuroxazide, SG-4-54, HO-3867, cryptotanshinone, cucurbitacin I, OPB-31121, resveratrol, pimozide, MS 1020, LLL12, and galiellactone.

In some embodiments, the inhibitor of JAK-STAT pathway is an inhibitor of STAT3. The inhibitor of STAT3 may be any inhibitor of STAT3 known in the art or as described herein. Examples of inhibitors STAT3 include, but are not limited to: cryptotanshinone, cucurbitacin I, niclosamide, NSC 74859, RSVA 405, SD 1008, stattic, BP-1-102, S31-201, STA-21, and SPI.

The JAK/STAT pathway is a major signaling mechanism for a diverse group of cytokines and growth factors (reviewed in Rawlings et al., 2004, J. Cell Sci., 117:1281). Binding of these ligands to their receptors induces multimerization of receptor subunits that are associated with Janus tyrosine kinases (JAKs), allowing transphosphorylation of the JAKs. Activated JAKs phosphorylate signal transducers and activators of transcription proteins (STATs), transcription factors that are present in the cytoplasm in latent form until activated. Phosphorylated STATs dimerize and are translocated into the nucleus, where they activate or repress transcription of target genes. In addition to these main components of the JAK/STAT pathway, other proteins that contribute to JAK/STAT signaling include signal-trans adapter molecules (STAMs), STAT-interacting protein (StIP), and the SH2B/Lnk/APS family. There are three main classes of negative regulators of JAK/STAT signaling: suppressor of cytokine signaling (SOCS) proteins, protein inhibitors of activated STATs (PIAS) proteins, and protein tyrosine phosphatases (PTPs).

Janus kinase (JAK) represents a family of intracellular, nonreceptor tyrosine kinases. They transduce cytokine-mediated signals via the JAK-STAT pathway. The family consists of four members: JAK1, JAK2, JAK3, and tyrosine kinase 2 (TYK2). They range from 120-140 kDa in size, and include seven regions of homology (Janus homology domains 1 to 7, JH1-7). JH1 is the kinase domain and includes the conserved tyrosines necessary for JAK activation. Phosphorylation of the dual tyrosines causes a conformation change in the JAK protein, allowing the substrate to bind. The amino terminal of the JAK (JH4-JH7) is involved in the association of JAKs with cytosine receptors and other kinases.

JAKs phosphorylate and activate downstream proteins of type I and type II cytokine receptor families. JAKs bind to the proline-rich domains of paired intracellular receptors. When the appropriate ligand binds the receptors, the receptors undergo a conformational change, bringing the two JAKs close enough so they can phosphorylate one another. This autophosphorylation causes a conformational change with allows the JAK to transduce the intracellular signal through the phosphorylation and activation of Signal Transducer and Activator of Transcription (STAT) transcription factors. An exemplary human JAK protein sequence is provided below:

(SEQ ID NO: 1)
MGMACLTMTEMEGTSTSSIYQNGDISGNANSMKQIDPVLQVYLYHSLGKS

EADYLTFPSGEYVAEEICIAASKACGITPVYHNMFALMSETERIWYPPNH

VFHIDESTRHNVLYRIRFYFPRWYCSGSNRAYRHGISRGAEAPLLDDFVM

SYLFAQWRHDFVHGWIKVPVTHETQEECLGMAVLDMMRIAKENDQTPLAI

YNSISYKTFLPKCIRAKIQDYHILTRKRIRYRFRRFIQQFSQCKATARNL

KLKYLINLETLQSAFYTEKFEVKEPGSGPSGEEIFATIIITGNGGIQWSR

GKHKESETLTEQDLQLYCDFPNIIDVSIKQANQEGSNESRVVTIHKQDGK

NLEIELSSLREALSFVSLIDGYYRLTADAHHYLCKEVAPPAVLENIQSNC

HGPISMDFAISKLKKAGNQTGLYVLRCSPKDFNKYFLTFAVERENVIEYK

HCLITKNENEEYNLSGTKKNFSSLKDLLNCYQMETVRSDNIIFQFTKCCP

PKPKDKSNLLVFRTNGVSDVPTSPTLQRPTHMNQMVFHKIRNEDLIFNES

LGQGTFTKIFKGVRREVGDYGQLHETEVLLKVLDKAHRNYSESFFEAASM

MSKLSHKHLVLNYGVCVCGDENILVQEFVKFGSLDTYLKKNKNCINILWK

LEVAKQLAWAMHFLEENTLIHGNVCAKNILLIREEDRKTGNPPFIKLSDP

GISITVLPKDILQERIPWVPPECIENPKNLNLATDKWSFGTTLWEICSGG

DKPLSALDSQRKLQFYEDRHQLPAPKWAELANLINNCMDYEPDFRPSFRA

IIRDLNSLFTPDYELLTENDMLPNMRIGALGFSGAFEDRDPTQFEERHLK

FLQQLGKGNFGSVEMCRYDPLQDNTGEVVAVKKLQHSTEEHLRDFEREIE

ILKSLQHDNIVKYKGVCYSAGRRNLKLIMEYLPYGSLRDYLQKHKERIDH

IKLLQYTSQICKGMEYLGTKRYIHRDLATRNILVENENRVKIGDFGLTKV

LPQDKEYYKVKEPGESPIFWYAPESLTESKFSVASDVWSFGVVLYELFTY

IEKSKSPPAEFMRMIGNDKQGQMIVFHLIELLKNNGRLPRPDGCPDEIYM

IMTECWNNNVNQRPSFRDLALRVDQIRDNMAG
(JAK2-NP_004963.1).

The Signal Transducer and Activator of Transcription (STAT) protein regulates aspects of cellular growth, survival, and differentiation. The STAT family includes STAT1, STAT2, STAT3, STAT4, STAT5 (STAT5A and STAT5B), and STAT6. STAT proteins exists in the cytosol and nucleus in an unphosphorylated state. On phosphorylation by JAK, STAT monomers dimerize via their SH2 domain and are then actively transported in the nucleus by the importin a/b and RanGDP complex. In the nucleus, the dimerized STAT binds to cytokine-inducible promoter regions of genes containing gamma-activated site (GAS) motifs, leading to the transcription of the gene. STATs are dephosphorylated and inactivated by nuclear phosphatases. An exemplary human STAT protein sequence is provided below:

(SEQ ID NO: 2)
MAQWEMLQNLDSPFQDQLHQLYSHSLLPVDIRQYLAVWIEDQNWQEAALG

SDDSKATMLFFHFLDQLNYECGRCSQDPESLLLQHNLRKFCRDIQPFSQD

PTQLAEMIFNLLLEEKRILIQAQRAQLEQGEPVLETPVESQQHEIESRIL

DLRAMMEKLVKSISQLKDQQDVFCFRYKIQAKGKTPSLDPHQTKEQKILQ

ETLNELDKRRKEVLDASKALLGRLTTLIELLLPKLEEWKAQQQKACIRAP

IDHGLEQLETWFTAGAKLLFHLRQLLKELKGLSCLVSYQDDPLTKGVDLR

NAQVTELLQRLLHRAFVVETQPCMPQTPHRPLILKTGSKFTVRTRLLVRL

QEGNESLTVEVSIDRNPPQLQGFRKFNILTSNQKTLTPEKGQSQGLIWDF

GYLTLVEQRSGGSGKGSNKGPLGVTEELHIISFTVKYTYQGLKQELKTDT

-continued

```
LPVVIISNMNQLSIAWASVLWFNLLSPNLQNQQFFSNPPKAPWSLLGPAL

SWQFSSYVGRGLNSDQLSMLRNKLFGQNCRTEDPLLSWADFTKRESPPGK

LPFWTWLDKILELVHDHLKDLWNDGRIMGFVSRSQERRLLKKTMSGTFLL

RFSESSEGGITCSWVEHQDDDKVLIYSVQPYTKEVLQSLPLTEIIRHYQL

LTEENIPENPLRFLYPRIPRDEAFGCYYQEKVNLQERRKYLKHRLIVVSN

RQVDELQQPLELKPEPELESLELELGLVPEPELSLDLEPLLKAGLDLGPE

LESVLESTLEPVIEPTLCMVSQTVPEPDQGPVSQPVPEPDLPCDLRHLNT

EPMEIFRNCVKIEEIMPNGDPLLAGQNTVDEVYVSRPSHFYTDGPLMPSD

F (STAT2-NP_005410.1).
```

Signal Transducer and Activator of Transcription 3 (STAT3) is a transcription factor that mediates the expression of a variety of genes in response to cell stimuli, playing a key role in many cellular processes, including cell growth and apoptosis. STAT3 is activated by the phosphorylation of tyrosine 705 in response to certain cytokines and growth factors. Some activators of STAT3 include the following: interferons, epidermal growth factor, interleukin-(IL) 5, IL-6, hepatocyte growth factor, leukemia inhibitory factor, bone morphogenetic protein 2, IL-10, and leptin. STAT3 may promote oncogenesis when it is constitutively active. It also may play a role in tumor suppression; in glioblastoma tumors, STAT3 was shown to suppress a tumor with a specific mutational background. An exemplary STAT3 human protein sequence is provided below:

```
                                                (SEQ ID NO: 3)
MAQWNQLQQLDTRYLEQLHQLYSDSFPMELRQFLAPWIESQDWAYAASKE

SHATLVFHNLLGEIDQQYSRFLQESNVLYQHNLRRIKQFLQSRYLEKPME

IARIVARCLWEESRLLQTAATAAQQGGQANHPTAAVVTEKQQMLEQHLQD

VRKRVQDLEQKMKVVENLQDDFDFNYKTLKSQGDMQDLNGNNQSVTRQKM

QQLEQMLTALDQMRRSIVSELAGLLSAMEYVQKTLTDEELADWKRRQQIA

CIGGPPNICLDRLENWITSLAESQLQTRQQIKKLEELQQKVSYKGDPIVQ

HRPMLEERIVELFRNLMKSAFVVERQPCMPMHPDRPLVIKTGVQFTTKVR

LLVKFPELNYQLKIKVCIDKDSGDVAALRGSRKFNILGTNTKVMNMEESN

NGSLSAEFKHLTLREQRCGNGGRANCDASLIVTEELHLITFETEVYHQGL

KIDLETHSLPVVVISNICQMPNAWASILWYNMLTNNPKNVNFFTKPPIGT

WDQVAEVLSWQFSSTTKRGLSIEQLTTLAEKLLGPGVNYSGCQITWAKFC

KENMAGKGFSFWVWLDNIIDLVKKYILALWNEGYIMGFISKERERAILST

KPPGTFLLRFSESSKEGGVTFTWVEKDISGKTQIQSVEPYTKQQLNNMSF

AEIIMGYKIMDATNILVSPLVYLYPDIPKEEAFGKYCRPESQEHPEADPG

SAAPYLKTKFICVTPTTCSNTIDLPMSPRTLDSLMQFGNNGEGAEPSAGG

QFESLTFDMELTSECATSPM (STAT3-NP_644805.1).
```

As used herein, "treat" or "treatment" of a myopathy includes, but is not limited to, preventing, reducing, or halting the development of a myopathy, reducing or eliminating the sign(s) and/or symptom(s) of a myopathy or results in a desired clinical effect. The primary symptom in myopathy is muscle weakness. Other symptoms of myopathy can include, for example, muscle cramps, stiffness, and spasm. Other manifestations of myopathy can also include, but are not limited to, hypotonia, delayed motor milestones, impaired ambulation, joint contractures, scoliosis, eye movement paralysis, respiratory insufficiency or failure, and malignant hyperthermia susceptibility. In some embodiments, treatment of a myopathy involves increasing or restoring muscle strength and/or restoration of muscle function and/or phenotype. Signs and symptoms of myopathy are known to those of ordinary skill in the art who know how to test for them and monitor their progression/regression.

The subject may be any subject, such as a human subject having a myopathy (e.g., a skeletal muscle myopathy). A myopathy is a disorder where the muscle fibers (e.g., skeletal muscle fibers) do not function properly, for any one of many reasons, leading to muscle weakness. Any type of myopathy is contemplated herein, including, but not limited to congenital myopathy, myofibrillar myopathy, endocrine or metabolic myopathy, toxic myopathy, or a myopathy caused by a systemic illness.

The congenital myopathies (CMs) are a heterogeneous group of inherited neuromuscular disorders that manifest as skeletal muscle weakness at birth or early in life, and are defined by the presence of specific morphological features on biopsy[1-3]. The most common forms of CM can be roughly subdivided into four categories based on the predominant pathologic features observed under light and electron microscopy: (i) centronuclear myopathies; (ii) core myopathies; (iii) nemaline (or rod) myopathies; and (iv) myopathies with congenital fiber type disproportion. However, accurate diagnoses are often confounded due to broad variations in the clinical severity of each phenotype, and to substantial histological overlap between the different forms of these disorders[4,5]. CMs can also result from mutations in more than one gene, with causative genes associated with multiple pathologies. Clinical features, such as the presentation of hypotonia during the newborn period, may be similar to features found in patients with congenital myasthenic syndromes, metabolic myopathies, spinal muscular atrophy, as well as muscular dystrophies. Thus, CMs are typically a diagnosis of exclusion and require detailed clinical data combined with electromyographic and histopathological findings to prioritize gene testing and establish a genetic basis[3,6].

Mutations of more than twenty known genes are capable of causing CM and their biological functions are widely studied in vitro and in vivo. Major pathophysiologic pathways responsible for weakness in CMs are hypothesized to result from either malformed contractile filaments, in the case of nemaline and other rod myopathies, or from disruptions in calcium homeostasis at the skeletal muscle triad, in the case of many centronuclear and core myopathies[1,7].

Centronuclear myopathies (CNMs) are classically defined by the abnormal centralization of nuclei in >25% of muscle fibers, although there can be considerable variability both in the number of myofibers with central nuclei and in the number of central nuclei within a single myofiber[8]. Several genetically distinct forms of CNM have been described based on age of onset, severity of symptoms, and mode of inheritance[9,10]. Clinically, these can be categorized as the severe X-linked recessive form with prenatal or neonatal onset, the autosomal recessive form with onset in infancy or childhood, and the autosomal dominant form, typically mild with late onset. Despite copious variability in the clinical features among these groups, emerging evidence suggests that defective excitation-contraction coupling at the level of the triad may be a unifying pathophysiological feature in CNM[11].

X-linked centronuclear myopathy, also referred to as myotubular myopathy or X-linked myotubular myopathy (XLMTM), is caused by mutations in the myotubularin (MTM1) gene[12]. Of the more than 500 known MTM1 mutations, most are believed to result in loss of protein expression, although there are a few recurring missense mutations that can cause either the classic severe phenotype or a milder presentation[13-15]. XLMTM may present prenatally with polyhydramnios and reduced fetal movements in utero, and in affected newborn boys as severe hypotonia, generalized weakness, and muscle wasting. Additional features include thin ribs, ophthalmoplegia, ptosis, pyloric stenosis, and contractures of the hips and knees. XLMTM carries a poor long-term prognosis, with death due to respiratory failure occurring within the first year of life in 20-25% of cases 16,17. Although a small proportion of boys may be less affected in the neonatal period and survive into childhood or even adulthood, most remain severely impaired and require permanent ventilation.

Mutations in the large GTPase dynamin 2 (DNM2) are the second most common cause of CNM and display dominant inheritance[18,19]. Autosomal dominant CNM showing late adult onset with slowly progressive weakness, together with de novo forms of CNM with earlier onset, has a broader range of clinical presentation than the X-linked form[19-21]. Generally, limb girdle, trunk, and neck muscles are involved, with degrees of ptosis and limitation of eye movements paralleling the age of onset. While most patients are ventilator independent, phases of respiratory decline may require non-invasive ventilation but rarely necessitate invasive support[22-26].

Autosomal recessive centronuclear myopathy is the rarest form of CNM, with causative mutations identified in the skeletal muscle ryanodine receptor (RYRP, titin (TTN), and bridging integrator 1 (BIN1) genes[27-29]. The recessive forms of the disease generally present in infancy or early childhood with diffuse muscle weakness and respiratory distress. Facial diplegia, ptosis, and varying degrees of ophthalmoplegia are also common features. The clinical course of the disease is marked by slowly progressive weakness, development of scoliosis or kyphosis, as well as delays in motor milestones such as walking, running, and stair climbing.

Core myopathies are characterized by areas in the muscle fiber lacking oxidative and glycolytic enzymatic activity. Central cores run along the length of the myofiber, whereas minicores are short zones of myofibrillar disorganization that are wider than they are long on longitudinal section. Based on the presence of these abnormal features, patients with core myopathies are traditionally sub-classified as having either central core disease (CCD) or multiminicore disease (MmD)[30]. The vast majority of CCD patients (>90%) have autosomal dominant or de novo dominant mutations in the RYR1 gene[31-34] while MmD core myopathy is most commonly caused by recessive mutations in the selenoprotein N gene (SEPN1) gene[35].

CCD was the first CM defined on the basis of specific morphological changes in skeletal muscle. In 1956, Magee and Shy described the first patient with single, well-circumscribed circular regions in the center of type I (slow twitch) fibers[36]. The term "central core disease" was introduced soon afterwards to reflect the absence of oxidative enzymes, phosphorylase, and glycogen in the core area due to mitochondrial depletion[37]. Whereas cores are best observed in sections stained for oxidative enzyme activity (e.g., succinate dehydrogenase [SDH], cytochrome-c-oxidase [COX], or nicotinamide adenine dinucleotide [NADH] dehydrogenase reacted sections), cores examined using electron microscopy contain densely packed and disorganized myofibrils, and have been divided into two types based on whether myofibrillar organization is maintained. Structured cores preserve basic sarcomeric architecture, although sarcomeres may be out of register with adjacent fibrils as well as with each other, whereas unstructured cores contain large areas of Z-line streaming[38]. Clinically, CCD typically presents in infancy with hypotonia or in early childhood with delays in motor development. Although weakness preferentially affects proximal musculature, such as hip girdle and axial muscles, almost all CCD patients achieve the ability to walk independently. The primary exceptions are cases with debilitating hip dislocations or severe cases presenting with neonatal weakness, arthrogryposis, and respiratory failure[34,39-42].

Fifteen years after the initial description of CCD, Engel and colleagues reported a family with two affected siblings exhibiting multiple small cores within muscle fibers[43]. Patients with the classic form of MmD generally present in infancy or childhood with pronounced hypotonia and proximal weakness, although select cases of prenatal or adult onset have been recognized[44-47]. Axial muscle weakness, particularly affecting the neck and trunk flexors, is a prominent feature of MmD, and failure to acquire head control is an early clinical sign. Spinal rigidity and scoliosis are also common. The clinical course of MmD is static for the majority of patients. However, some experience cardiac involvement secondary to marked decline in respiratory function during adolescence or young adulthood[44].

MmD is diagnosed on muscle biopsy by the presence of multifocal, well-circumscribed areas in the muscle fiber with reduced oxidative staining and low myofibrillar ATPase activity[43]. In contrast to central cores, "minicores" are typically unstructured, extend for only a short distance along the longitudinal axis of the myofiber, and may affect both type I (slow twitch) and type II (fast twitch) fibers[48]. Minicores appear as regions of myofibrillar disruption lacking mitochondria in electron micrographs, with sarcomere degeneration and structural abnormalities of the triad.

Core-rod myopathy is a congenital myopathy characterized by the presence of "cores" and "rods" in distinct locations within the same or different muscle fibers, and has been reported in a small number of sporadic or familial cases. Familial cases have been associated with mutations in the skeletal muscle RYR1, nebulin (NEB), and alpha-actin (ACTA1) genes.

Clinically, nemaline myopathy (NM) phenotypes vary and are sub-classified into different groups according to age of onset as well as severity of motor and respiratory involvement: (i) severe congenital NM, (ii) intermediate congenital NM, (iii) typical congenital NM, (iv) childhood/juvenile-onset NM, (v) adult-onset NM, and (vi) other forms with atypical clinical features such as cardiomyopathy and ophthalmoplegia[49]. Although these classifications have been well established and can be used to accurately predict prognosis, certain morphological and clinical features are common and shared between two or more groups. Nemaline rods, for example, are the pathological and diagnostic hallmark of NM, and by definition are shared among all genetic forms of this disorder.

Rods appear as red or purple structures against a blue-green myofibrillar background upon modified Gömöri trichrome staining, and show a tendency to cluster under the sarcolemma and around nuclei. Rods are considered to derive from the lateral expansion of the Z-line, based on their structural continuity with Z-lines, electron density, and criss-cross pattern in electron micrographs. Rods also stain positively for antibodies to alpha-actinin isoforms 2 and 3, the two major components of the skeletal muscle Z-line[50,51]. With few exceptions (e.g., patients with TPM3 mutations), rods are present in both type I and type II muscle fibers, although type I fiber predominance is a common feature of NM and fiber type disproportions tend to become more prominent with age[52,53]. The proportion of myofibers containing rods varies considerably between cases, however, and the sizes and numbers of rods within a muscle specimen do not appear to correlate with disease severity[54]. Nemaline rods are usually cytoplasmic. Intranuclear rods are occasionally a prominent feature, particularly in severe cases[55].

NMs are considered diseases in which mutations disrupt the ability of the myofiber to generate adequate force during contraction. To date, mutations in ten different genes have been identified in a subset of NM patients: alpha-skeletal muscle actin (ACTA1)[56]; slow alpha-tropomyosin (TPM3)[57-59]; nebulin (NEB)[60]; slow troponin T (TNNT1)[61,62]; beta-tropomyosin (TPM2)[59,63]; muscle-specific cofilin (CFL2)[64-66]; leiomodin 3 (LMOD3)[67]; kelch-like family members 40 (KLHL40)[68] and 41 (KLHL41)[69]; and kelch repeat and BTB domain containing 13 (KBTBD13)[70]. Seven of these ten genes encode protein components of the muscle fiber thin filament, while the other three likely participate as regulators of the thin filament degradation/turnover apparatus.

Congenital fiber type disproportion (CFTD) is a histological diagnosis with multiple etiologies[71]. Brooke and Engel first used the term in 1973 in a large morphology study of children's biopsies to describe a group of 14 patients who all had clinical features of a CM and whose prevalent abnormality on muscle biopsy was a discrepancy in muscle fiber size[72]. It is now the consensus that the diagnosis of CFTD can be made when a mutation in a CM gene has been identified and type I fibers are consistently smaller than type II fibers by at least 35-40%[73]. However, type I fiber hypotrophy is also observed in a variety of metabolic myopathies, in central nervous system malformations, and in the severe neonatal form of myotonic muscular dystrophy[74-78]. Some experts therefore include additional histologic features in the definition of CFTD, such as type I fiber predominance (>55% type I fibers) or a paucity (<5%) of type IIB fibers[73]. While CFTD generally mimics the clinical course of other forms of CM that share the same genetic cause, early respiratory failure is frequent among CFTD patients and nocturnal hypoventilation should be monitored even in ambulant individuals[2].

Most cases of CFTD are associated with mutations in the TPM3 gene, encoding the type I fiber-specific protein slow alpha-tropomyosin[79-81]. TPM3 mutations are hypothesized to alter the interaction between tropomyosin and actin[79], and some data suggest that clinical weakness may arise from misregulated acting myosin interactions[82]. RYR1 mutations are less commonly seen[83] and only rarely have mutations in ACTA1[84], MYH7[85,86], SEPN1[87], TPM2[88], or an X-linked form[89] been reported. Most recently, mutations of the LMNA gene, coding for lamin A/C, were identified in several Japanese patients with CFTD[90]. Since LMNA defects are known to cause a variety of different muscular dystrophies and related cardiomyopathies[91], these patients may represent a subset of CFTD cases at risk for cardiac disease.

The CM may be a ryanodine receptor 1 (RYR1)-related myopathy[92]. RYR1-related myopathies are defined as a group of inherited disorders associated with causative mutations in the skeletal muscle RYR1 gene (RYR1). Although age of clinical onset is variable, patients with RYR1 mutations typically present with skeletal muscle weakness in infancy or early childhood. Other manifestations can also include, but are not limited to, delayed motor milestones, impaired ambulation, joint contractures, scoliosis, eye movement paralysis, respiratory failure, and malignant hyperthermia susceptibility. Examples of RYR1-related myopathies include, for example, CCD, CFTD, CNM, MmD, NM, and core-rod myopathy.

The myofibrillar myopathies are a clinically and genetically heterogeneous group of disorders defined by the presence of focal myofibrillar disarray and desmin-positive myofibrillar aggregates on muscle biopsy. Myofibrillar myopathies are primarily a disorder of adulthood, but their age of onset ranges from early childhood to middle age, and does include a severe, progressive childhood presentation. Weakness is most commonly distal, or may be more diffuse, and bulbar or respiratory involvement occurs in some families. Cardiac symptoms may dominate the clinical picture, particularly hypertrophic cardiomyopathy or atrioventricular conduction block. Lens opacities and neuropathic features have also been reported in some families.

Endocrine and metabolic myopathies result in muscle fatigue and weakness, frequently shown as muscle atrophy. Endocrine myopathies include myopathies caused but are not limited to, thyroid disorders, including hypothyroidism and hyperthyroidism, parathyroid disorders, including hyperparathyroidism and hypoparathyroidism, adrenal disorders, and pituitary disorders. Metabolic myopathies, include, myopathies caused but are not limited to, diabetes mellitus, and a vitamin deficiency.

Myopathies resulting from systemic illnesses often result in fatigue, muscle wasting, and weakness. Exemplary systemic illnesses causing myopathies include chronic respiratory, cardiac, and hepatic failure. Chronic renal failure may also result in myopathy, independent of uremic polyneuropathy. The resulting calcium and phosphorus homeostasis abnormalities, as well as bone metabolism irregularities may lead to the development of hypocalcemia augmented by hyperphosphatemia, causing secondary hyperparathyroidism. The compensatory hyperparathyroidism then yields renal osteodystrophy, osteomalacia, and osteitis fibrosa. Chronic renal failure can also lead to gangrenous calcification; extensive arterial calcification results in ischemia, myopathy, and skin necrosis.

Toxic myopathies occur when drugs and chemicals produce damage to skeletal muscle. Focal damage is typically caused by the injection of narcotic analgesics, for example, pentazocine, meperidine, or heroin. Injections may cause severe fibrotic reactions in the muscle, the formation of local abscesses, and cutaneous ulcerations and depressions. Other drugs can lead to generalized muscle weakness, specifically in the proximal muscles. Examples include propranolol, cyclosporine, iodines, clofibrate, chloroquine, gemfibrozil, HMG-CoA reductase inhibitors (e.g., statins such as atorvastatin (Lipitor®), fluvastatin (Lescol®), lovastatin (Mevacor®, Altocor®), pitavastatin (Livalo®), pravastatin (Pravachol®), rosuvastatin (Crestor®), and simvastatin (Zocor®)), niacin, colchicine, cyclosporine, emetine, ε-amino-caproic acid, glucocorticoids, labetalol, perhexilline, propranolol, vincristine, zidovudine, alcohol, amphetamine, barbiturates, cocaine, heroin, and phencyclidine.

Subjects having a myopathy may be identified using any method known in the art (including, but not limited to, physical examination, strength testing, skeletal muscle biopsy with histology, immunohistochemistry, and/or electron microscopy, electromyogram, blood test(s), CT scan, X-ray, MRI, physical exam, cytogenetic analysis, urinalysis, or genetic testing). A subject suspected of having a myopathy might show one or more sign(s) or symptom(s) of the disease. Signs and symptoms of myopathies are well known to those of ordinary skill in the art.

The inhibitor of JAK-STAT pathway, JAK, STAT, or STAT3 may be any inhibitor of JAK-STAT pathway, JAK, STAT, or STAT3 known in the art or described herein. The inhibitor may reduce the level and/or activity of JAK-STAT pathway, JAK, STAT, or STAT3. A reduced level of one or more of JAK-STAT pathway, JAK, STAT, or STAT3 includes a level that is, for example, 1%, 5%, 10%, 20%, 30%, 40%, 50%, 60%, 70%, 80%, 90%, 100%, 150%, 200%, 300%, 400%, 500% or more below a control level. In some embodiments, the level is reduced to a level that is undetectable. Levels of JAK, STAT, or STAT3 (e.g., mRNA level or protein level) can be measured using a method known in the art or described herein, such as by Northern blot analysis, q.RT-PCR, sequencing technology, RNA in situ hybridization, in situ RT-PCR, oligonucleotide microarray, immunoassays (e.g., Western blot, immunohistochemistry and ELISA assays), Mass spectrometry, or multiplex bead-based assays.

In some embodiments, the inhibitor is a small molecule, an antisense oligonucleotide, a small interfering RNA (siRNA), a microRNA (miRNA), or an antibody. Methods of making such inhibitors are known in the art. The antibody may be a full-length antibody or an antigen-binding fragment thereof, such as a Fab, F(ab)2, Fv, single chain antibody, Fab or sFab fragment, F(ab')2, Fd fragments, scFv, or dAb fragments. Methods for producing antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609). The small molecule may be, in some embodiments, an organic compound having a molecular weight of below 900, below 800, below 700, below 600, or below 500 daltons. Methods of making such small molecules are known in the art. Antisense oligonucleotides may be modified or unmodified single-stranded DNA molecules of less than 50 nucleotides in length (e.g., 13-25 nucleotides in length). siRNAs may be double-stranded RNA molecules of about 19-25 base pairs in length with optional 3' dinucleotide overhangs on each strand. Antisense oligonucleotides and siRNAs are generally made by chemical synthesis methods that are known in the art. MicroRNAs (miRNAs) are small non-coding RNA molecules. They may be transcribed and then processed from a primary-microRNA (pri-miRNA) to a progenitor-microRNA (pro-miRNA) to a pre-microRNA (pre-miRNA), and finally to a mature miRNA, which can act as an inhibitor. miRNAs may be produced in a subject by delivering a gene that encodes the pri-miRNA, which is then processed in the subject to a mature miRNA.

An effective amount of an agent or inhibitor as described herein is an amount that is sufficient to provide a medically desirable result, such as treatment of a myopathy (e.g., manifestation(s), or sign(s) and/or symptom(s) of a myopathy). The effective amount will vary with the particular myopathy being treated, the age and physical condition of the subject being treated, the severity of the condition, the duration of the treatment, the nature of any concurrent therapy, the specific route of administration and the like factors within the knowledge and expertise of the health practitioner. For administration to a subject such as a human, a dosage of from about 0.001, 0.01, 0.1, or 1 mg/kg up to 50, 100, 150, or 500 mg/kg or more can typically be employed.

An agent or inhibitor as described herein and compositions thereof can be formulated for a variety of modes of administration, including systemic, topical or localized administration. A variety of administration routes are available. The particular mode selected will depend upon the type of myopathy or other disease being treated and the dosage required for therapeutic efficacy. The methods of the disclosure, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, or parenteral routes. The term "parenteral" includes subcutaneous, intravenous, intramuscular, or infusion.

Techniques and formulations generally can be found in Remington: The Science and Practice of Pharmacy, Pharmaceutical Press; 22nd edition and other similar references. When administered, an agent or inhibitor as described herein may be applied in pharmaceutically-acceptable amounts and in pharmaceutically-acceptable compositions. Pharmaceutical compositions and pharmaceutically-acceptable carriers are also described herein. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the disclosure. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Compositions and Pharmaceutically-Acceptable Carriers

Other aspects of the disclosure relate to compositions comprising an agent or inhibitor as described herein, e.g., for use in treatment of a myopathy. In some embodiments, the composition is a pharmaceutical composition. In some embodiments, the composition comprises an agent or inhibitor as described herein and a pharmaceutically-acceptable carrier. In some embodiments, the composition is for use in treating a myopathy.

The term "pharmaceutically-acceptable carrier" as used herein means one or more compatible solid or liquid filler, diluents or encapsulating substances which are suitable for administration into a subject, e.g., a human. A pharmaceutically acceptable carrier is "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the pharmaceutical compositions also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the composition.

The pharmaceutical compositions may conveniently be presented in unit dosage form and may be prepared by any of the methods well-known in the art of pharmacy. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

The formulation of the pharmaceutical composition may depend upon the route of administration. Injectable preparations suitable for parenteral administration or intratumoral, peritumoral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

For topical administration, the pharmaceutical composition can be formulated into ointments, salves, gels, or creams, as is generally known in the art. Topical administration can utilize transdermal delivery systems well known in the art. An example is a dermal patch.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the agent or inhibitor, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The agent or inhibitor described herein and/or the pharmaceutical composition ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

REFERENCES FOR DETAILED DESCRIPTION
OF THE INVENTION

1. Nance, J. R., Dowling, J. J., Gibbs, E. M. and Bonnemann, C. G. (2012) Congenital myopathies: an update. Curr Neurol Neurosci Rep, 12, 165-174.
2. Romero, N. B. and Clarke, N. F. (2013) Congenital myopathies. Handb Clin Neurol, 113, 1321-1336.
3. North, K. N., Wang, C. H., Clarke, N., Jungbluth, H., Vainzof, M., Dowling, J. J., Amburgey, K., Quijano-Roy, S., Beggs, A. H., Sewry, C. et al. (2014) Approach to the diagnosis of congenital myopathies. Neuromuscul Disord, 24, 97-116.

4. Ryan, M. M., Schnell, C., Strickland, C. D., Shield, L. K., Morgan, G., Iannaccone, S. T., Laing, N. G., Beggs, A. H. and North, K. N. (2001) Nemaline myopathy: a clinical study of 143 cases. Ann Neurol, 50, 312-320.

5. Romero, N. B., Monnier, N., Viollet, L., Cortey, A., Chevallay, M., Leroy, J. P., Lunardi, J. and Fardeau, M. (2003) Dominant and recessive central core disease associated with RYR1 mutations and fetal akinesia. Brain, 126, 2341-2349.

6. North, K. N. (2011) Clinical approach to the diagnosis of congenital myopathies. Semin Pediatr Neurol, 18, 216-220.

7. Al-Qusairi, L. and Laporte, J. (2011) T-tubule biogenesis and triad formation in skeletal muscle and implication in human diseases. Skelet Muscle, 1, 26.

8. Pierson, C. R., Tomczak, K., Agrawal, P., Moghadaszadeh, B. and Beggs, A. H. (2005) X-linked myotubular and centronuclear myopathies. J Neuropathol Exp Neurol, 64, 555-564.

9. Romero, N. B. and Bitoun, M. (2011) Centronuclear myopathies. Semin Pediatr Neurol, 18, 250-256.

10. Biancalana, V., Beggs, A. H., Das, S., Jungbluth, H., Kress, W., Nishino, I., North, K., Romero, N. B. and Laporte, J. (2012) Clinical utility gene card for: Centronuclear and myotubular myopathies. Eur J Hum Genet, 20.

11. Jungbluth, H. and Gautel, M. (2014) Pathogenic mechanisms in centronuclear myopathies. Front Aging Neurosci, 6, 339.

12. Laporte, J., Hu, L. J., Kretz, C., Mandel, J. L., Kioschis, P., Coy, J. F., Klauck, S. M., Poustka, A. and Dahl, N. (1996) A gene mutated in X-linked myotubular myopathy defines a new putative tyrosine phosphatase family conserved in yeast. Nat Genet, 13, 175-182.

13. Biancalana, V., Caron, O., Gallati, S., Baas, F., Kress, W., Novelli, G., D'Apice, M. R., Lagier-Tourenne, C., Buj-Bello, A., Romero, N. B. et al. (2003) Characterisation of mutations in 77 patients with X-linked myotubular myopathy, including a family with a very mild phenotype. Hum Genet, 112, 135-142.

14. Pierson, C. R., Agrawal, P. B., Blasko, J. and Beggs, A. H. (2007) Myofiber size correlates with MTM1 mutation type and outcome in X-linked myotubular myopathy. Neuromuscul Disord, 17, 562-568.

15. Oliveira, J., Oliveira, M. E., Kress, W., Taipa, R., Pires, M. M., Hilbert, P., Baxter, P., Santos, M., Buermans, H., den Dunnen, J. T. et al. (2013) Expanding the MTM1 mutational spectrum: novel variants including the first multi-exonic duplication and development of a locus-specific database. Eur J Hum Genet, 21, 540-549.

16. Herman, G. E., Finegold, M., Zhao, W., de Gouyon, B. and Metzenberg, A. (1999) Medical complications in long-term survivors with X-linked myotubular myopathy. J Pediatr, 134, 206-214.

17. McEntagart, M., Parsons, G., Buj-Bello, A., Biancalana, V., Fenton, I., Little, M., Krawczak, M., Thomas, N., Herman, G., Clarke, A. et al. (2002) Genotype-phenotype correlations in X-linked myotubular myopathy. Neuromuscul Disord, 12, 939-946.

18. Bitoun, M., Maugenre, S., Jeannet, P. Y., Lacene, E., Ferrer, X., Laforet, P., Martin, J. J., Laporte, J., Lochmuller, H., Beggs, A. H. et al. (2005) Mutations in dynamin 2 cause dominant centronuclear myopathy. Nat Genet, 37, 1207-1209.

19. Bohm, J., Biancalana, V., Dechene, E. T., Bitoun, M., Pierson, C. R., Schaefer, E., Karasoy, H., Dempsey, M. A., Klein, F., Dondaine, N. et al. (2012) Mutation spectrum in the large GTPase dynamin 2, and genotype-phenotype correlation in autosomal dominant centronuclear myopathy. Hum Mutat, 33, 949-959.

20. Jeannet, P. Y., Bassez, G., Eymard, B., Laforet, P., Urtizberea, J. A., Rouche, A., Guicheney, P., Fardeau, M. and Romero, N. B. (2004) Clinical and histologic findings in autosomal centronuclear myopathy. Neurology, 62, 1484-1490.

21. Hanisch, F., Muller, T., Dietz, A., Bitoun, M., Kress, W., Weis, J., Stoltenburg, G. and Zierz, S. (2011) Phenotype variability and histopathological findings in centronuclear myopathy due to DNM2 mutations. J Neurol, 258, 1085-1090.

22. McLeod, J. G., Baker Wde, C., Lethlean, A. K. and Shorey, C. D. (1972) Centronuclear myopathy with autosomal dominant inheritance. J Neurol Sci, 15, 375-387.

23. Wallgren-Pettersson, C., Clarke, A., Samson, F., Fardeau, M., Dubowitz, V., Moser, H., Grimm, T., Barohn, R. J. and Barth, P. G. (1995) The myotubular myopathies: differential diagnosis of the X linked recessive, autosomal dominant, and autosomal recessive forms and present state of DNA studies. J Med Genet, 32, 673-679.

24. Fischer, D., Herasse, M., Bitoun, M., Barragan-Campos, H. M., Chiras, J., Laforet, P., Fardeau, M., Eymard, B., Guicheney, P. and Romero, N. B. (2006) Characterization of the muscle involvement in dynamin 2-related centronuclear myopathy. Brain, 129, 1463-1469.

25. Bitoun, M., Bevilacqua, J. A., Prudhon, B., Maugenre, S., Taratuto, A. L., Monges, S., Lubieniecki, F., Cances, C., Uro-Coste, E., Mayer, M. et al. (2007) Dynamin 2 mutations cause sporadic centronuclear myopathy with neonatal onset. Ann Neurol, 62, 666-670.

26. Susman, R. D., Quijano-Roy, S., Yang, N., Webster, R., Clarke, N. F., Dowling, J., Kennerson, M., Nicholson, G., Biancalana, V., Ilkovski, B. et al. (2010) Expanding the clinical, pathological and MRI phenotype of DNM2-related centronuclear myopathy. Neuromuscul Disord, 20, 229-237.

27. Nicot, A. S., Toussaint, A., Tosch, V., Kretz, C., Wallgren-Pettersson, C., Iwarsson, E., Kingston, H., Garnier, J. M., Biancalana, V., Oldfors, A. et al. (2007) Mutations in amphiphysin 2 (BIN1) disrupt interaction with dynamin 2 and cause autosomal recessive centronuclear myopathy. Nat Genet, 39, 1134-1139.

28. Wilmshurst, J. M., Lillis, S., Zhou, H., Pillay, K., Henderson, H., Kress, W., Muller, C. R., Ndondo, A., Cloke, V., Cullup, T. et al. (2010) RYR1 mutations are a common cause of congenital myopathies with central nuclei. Ann Neurol, 68, 717-726.

29. Ceyhan-Birsoy, O., Agrawal, P. B., Hidalgo, C., Schmitz-Abe, K., DeChene, E. T., Swanson, L. C., Soemedi, R., Vasli, N., Iannaccone, S. T., Shieh, P. B. et al. (2013) Recessive truncating titin gene, TTN, mutations presenting as centronuclear myopathy. Neurology, 81, 1205-1214.

30. Jungbluth, H., Sewry, C. A. and Muntoni, F. (2011) Core myopathies. Semin Pediatr Neurol, 18, 239-249.

31. Lynch, P. J., Tong, J., Lehane, M., Mallet, A., Giblin, L., Heffron, J. J., Vaughan, P., Zafra, G., MacLennan, D. H. and McCarthy, T. V. (1999) A mutation in the transmembrane/luminal domain of the ryanodine receptor is associated with abnormal Ca2+ release channel function and severe central core disease. Proc Natl Acad Sci USA, 96, 4164-4169.
32. Monnier, N., Romero, N. B., Lerale, J., Nivoche, Y., Qi, D., MacLennan, D. H., Fardeau, M. and Lunardi, J. (2000) An autosomal dominant congenital myopathy with cores and rods is associated with a neomutation in the RYR1 gene encoding the skeletal muscle ryanodine receptor. Hum Mol Genet, 9, 2599-2608.
33. Davis, M. R., Haan, E., Jungbluth, H., Sewry, C., North, K., Muntoni, F., Kuntzer, T., Lamont, P., Bankier, A., Tomlinson, P. et al. (2003) Principal mutation hotspot for central core disease and related myopathies in the C-terminal transmembrane region of the RYR1 gene. Neuromuscul Disord, 13, 151-157.
34. Klein, A., Lillis, S., Munteanu, I., Scoto, M., Zhou, H., Quinlivan, R., Straub, V., Manzur, A. Y., Roper, H., Jeannet, P. Y. et al. (2012) Clinical and genetic findings in a large cohort of patients with ryanodine receptor 1 gene-associated myopathies. Hum Mutat, 33, 981-988.
35. Ferreiro, A., Quijano-Roy, S., Pichereau, C., Moghadaszadeh, B., Goemans, N., Bonnemann, C., Jungbluth, H., Straub, V., Villanova, M., Leroy, J. P. et al. (2002) Mutations of the selenoprotein N gene, which is implicated in rigid spine muscular dystrophy, cause the classical phenotype of multiminicore disease: reassessing the nosology of early-onset myopathies. Am J Hum Genet, 71, 739-749.
36. Magee, K. R. and Shy, G. M. (1956) A new congenital non-progressive myopathy. Brain, 79, 610-621.
37. Greenfield, J. G., Cornman, T. and Shy, G. M. (1958) The prognostic value of the muscle biopsy in the floppy infant. Brain, 81, 461-484.
38. Hayashi, K., Miller, R. G. and Brownell, A. K. (1989) Central core disease: ultrastructure of the sarcoplasmic reticulum and T-tubules. Muscle Nerve, 12, 95-102.
39. Dubowitz, V. (1995) Muscle Disorders in Childhood. Elsevier Health Sciences.
40. Manzur, A. Y., Sewry, C. A., Ziprin, J., Dubowitz, V. and Muntoni, F. (1998) A severe clinical and pathological variant of central core disease with possible autosomal recessive inheritance. Neuromuscul Disord, 8, 467-473.
41. Jungbluth, H., Muller, C. R., Halliger-Keller, B., Brockington, M., Brown, S. C., Feng, L., Chattopadhyay, A., Mercuri, E., Manzur, A. Y., Ferreiro, A. et al. (2002) Autosomal recessive inheritance of RYR1 mutations in a congenital myopathy with cores. Neurology, 59, 284-287.
42. Jungbluth, H. (2007) Central core disease. Orphanet J Rare Dis, 2, 25.
43. Engel, A. G., Gomez, M. R. and Groover, R. V. (1971) Multicore disease. A recently recognized congenital myopathy associated with multifocal degeneration of muscle fibers. Mayo Clin Proc, 46, 666-681.
44. Jungbluth, H., Sewry, C., Brown, S. C., Manzur, A. Y., Mercuri, E., Bushby, K., Rowe, P., Johnson, M. A., Hughes, I., Kelsey, A. et al. (2000) Minicore myopathy in children: a clinical and histopathological study of 19 cases. Neuromuscul Disord, 10, 264-273.
45. Ferreiro, A., Estournet, B., Chateau, D., Romero, N. B., Laroche, C., Odent, S., Toutain, A., Cabello, A., Fontan, D., dos Santos, H. G. et al. (2000) Multi-minicore disease—searching for boundaries: phenotype analysis of 38 cases. Ann Neurol, 48, 745-757.
46. Ferreiro, A., Monnier, N., Romero, N. B., Leroy, J. P., Bonnemann, C., Haenggeli, C. A., Straub, V., Voss, W. D., Nivoche, Y., Jungbluth, H. et al. (2002) A recessive form of central core disease, transiently presenting as multiminicore disease, is associated with a homozygous mutation in the ryanodine receptor type 1 gene. Ann Neurol, 51, 750-759.
47. Ferreiro, A. and Fardeau, M. (2002) 80th ENMC International Workshop on Multi-Minicore Disease: 1st International MmD Workshop. 12-13th May, 2000, Soestduinen, The Netherlands. Neuromuscul Disord, 12, 60-68.
48. Dubowitz, V. and Sewry, C. (2006) Muscle Biopsy: A Practical Approach. Elsevier-Health Sciences Division.
49. Wallgren-Pettersson, C. and Laing, N. G. (2000) Report of the 70th ENMC International Workshop: nemaline myopathy, 11-13 Jun. 1999, Naarden, The Netherlands. Neuromuscul Disord, 10, 299-306.
50. Jockusch, B. M., Veldman, H., Griffiths, G. W., van Oost, B. A. and Jennekens, F. G. (1980) Immunofluorescence microscopy of a myopathy. alpha-actinin is a major constituent of nemaline rods. Exp Cell Res, 127, 409-420.
51. Wallgren-Pettersson, C., Jasani, B., Newman, G. R., Morris, G. E., Jones, S., Singhrao, S., Clarke, A., Virtanen, I., Holmberg, C. and Rapola, J. (1995) Alpha-actinin in nemaline bodies in congenital nemaline myopathy: immunological confirmation by light and electron microscopy. Neuromuscul Disord, 5, 93-104.
52. Volpe, P., Damiani, E., Margreth, A., Pellegrini, G. and Scarlato, G. (1982) Fast to slow change of myosin in nemaline myopathy: electrophoretic and immunologic evidence. Neurology, 32, 37-41.
53. Miike, T., Ohtani, Y., Tamari, H., Ishitsu, T. and Une, Y. (1986) Muscle fiber type transformation in nemaline myopathy and congenital fiber type disproportion. Brain Dev, 8, 526-532.
54. Ryan, M. M., Ilkovski, B., Strickland, C. D., Schnell, C., Sanoudou, D., Midgett, C., Houston, R., Muirhead, D., Dennett, X., Shield, L. K. et al. (2003) Clinical course correlates poorly with muscle pathology in nemaline myopathy. Neurology, 60, 665-673.
55. Goebel, H. H. and Warlo, I. (1997) Nemaline myopathy with intranuclear rods—intranuclear rod myopathy. Neuromuscul Disord, 7, 13-19.
56. Nowak, K. J., Wattanasirichaigoon, D., Goebel, H. H., Wilce, M., Pelin, K., Donner, K., Jacob, R. L., Hubner, C., Oexle, K., Anderson, J. R. et al. (1999) Mutations in the skeletal muscle alpha-actin gene in patients with actin myopathy and nemaline myopathy. Nat Genet, 23, 208-212.
57. Laing, N. G., Wilton, S. D., Akkari, P. A., Dorosz, S., Boundy, K., Kneebone, C., Blumbergs, P., White, S., Watkins, H., Love, D. R. et al. (1995) A mutation in the alpha tropomyosin gene TPM3 associated with autosomal dominant nemaline myopathy. Nat Genet, 9, 75-79.
58. Wattanasirichaigoon, D., Swoboda, K. J., Takada, F., Tong, H. Q., Lip, V., Iannaccone, S. T., Wallgren-Pettersson, C., Laing, N. G. and Beggs, A. H. (2002) Mutations of the slow muscle alpha-tropomyosin gene, TPM3, are a rare cause of nemaline myopathy. Neurology, 59, 613-617.
59. Marttila, M., Lehtokari, V. L., Marston, S., Nyman, T. A., Barnerias, C., Beggs, A. H., Bertini, E., Ceyhan-Birsoy, O., Cintas, P., Gerard, M. et al. (2014) Mutation update and genotype-phenotype correlations of novel and previously described mutations in TPM2 and TPM3 causing congenital myopathies. Hum Mutat, 35, 779-790.
60. Pelin, K., Hilpela, P., Donner, K., Sewry, C., Akkari, P. A., Wilton, S. D., Wattanasirichaigoon, D., Bang, M. L., Centner, T., Hanefeld, F. et al. (1999) Mutations in the nebulin gene associated with autosomal recessive nemaline myopathy. Proc Natl Acad Sci USA, 96, 2305-2310.

61. Johnston, J. J., Kelley, R. I., Crawford, T. O., Morton, D. H., Agarwala, R., Koch, T., Schaffer, A. A., Francomano, C. A. and Biesecker, L. G. (2000) A novel nemaline myopathy in the Amish caused by a mutation in troponin T1. Am J Hum Genet, 67, 814-821.

62. van der Pol, W. L., Leijenaar, J. F., Spliet, W. G., Lavrijsen, S. W., Jansen, N.J., Braun, K. P., Mulder, M., Timmers-Raaijmakers, B., Ratsma, K., Dooijes, D. et al. (2014) Nemaline myopathy caused by TNNT1 mutations in a Dutch pedigree. Mol Genet Genomic Med, 2, 134-137.

63. Donner, K., Ollikainen, M., Ridanpaa, M., Christen, H. J., Goebel, H. H., de Visser, M., Pelin, K. and Wallgren-Pettersson, C. (2002) Mutations in the beta-tropomyosin (TPM2) gene—a rare cause of nemaline myopathy. Neuromuscul Disord, 12, 151-158.

64. Agrawal, P. B., Greenleaf, R. S., Tomczak, K. K., Lehtokari, V. L., Wallgren-Pettersson, C., Wallefeld, W., Laing, N. G., Darras, B. T., Maciver, S. K., Dormitzer, P. R. et al. (2007) Nemaline myopathy with minicores caused by mutation of the CFL2 gene encoding the skeletal muscle actin-binding protein, cofilin-2. Am J Hum Genet, 80, 162-167.

65. Ockeloen, C. W., Gilhuis, H. J., Pfundt, R., Kamsteeg, E. J., Agrawal, P. B., Beggs, A. H., Dara Hama-Amin, A., Diekstra, A., Knoers, N. V., Lammens, M. et al. (2012) Congenital myopathy caused by a novel missense mutation in the CFL2 gene. Neuromuscul Disord, 22, 632-639.

66. Ong, R. W., AlSaman, A., Selcen, D., Arabshahi, A., Yau, K. S., Ravenscroft, G., Duff, R. M., Atkinson, V., Allcock, R. J. and Laing, N. G. (2014) Novel cofilin-2 (CFL2) four base pair deletion causing nemaline myopathy. J Neurol Neurosurg Psychiatry, 85, 1058-1060.

67. Yuen, M., Sandaradura, S. A., Dowling, J. J., Kostyukova, A. S., Moroz, N., Quinlan, K. G., Lehtokari, V. L., Ravenscroft, G., Todd, E. J., Ceyhan-Birsoy, O. et al. (2014) Leiomodin-3 dysfunction results in thin filament disorganization and nemaline myopathy. J Clin Invest.

68. Ravenscroft, G., Miyatake, S., Lehtokari, V. L., Todd, E. J., Vornanen, P., Yau, K. S., Hayashi, Y. K., Miyake, N., Tsurusaki, Y., Doi, H. et al. (2013) Mutations in KLHL40 are a frequent cause of severe autosomal-recessive nemaline myopathy. Am J Hum Genet, 93, 6-18.

69. Gupta, V. A., Ravenscroft, G., Shaheen, R., Todd, E. J., Swanson, L. C., Shiina, M., Ogata, K., Hsu, C., Clarke, N. F., Darras, B. T. et al. (2013) Identification of KLHL41 mutations implicates BTB-kelch-mediated ubiquitination as an alternate pathway to myofibrillar disruption in nemaline myopathy. Am J Hum Genet, 93, 1108-1117.

70. Sambuughin, N., Yau, K. S., Olive, M., Duff, R. M., Bayarsaikhan, M., Lu, S., Gonzalez-Mera, L., Sivadorai, P., Nowak, K. J., Ravenscroft, G. et al. (2010) Dominant mutations in KBTBD13, a member of the BTB/Kelch family, cause nemaline myopathy with cores. Am J Hum Genet, 87, 842-847.

71. DeChene, E. T., Kang, P. B. and Beggs, A. H. (1993) Congenital fiber-type disproportion. In Pagon, R. A., Adam, M. P., Ardinger, H. H., Bird, T. D., Dolan, C. R., Fong, C. T., Smith, R. J. H. and Stephens, K. (eds.), In GeneReviews®, Seattle (Wash.).

72. Brooke, M. H. and Engel, W. K. (1969) The histographic analysis of human muscle biopsies with regard to fiber types. 4. Children's biopsies. Neurology, 19, 591-605.

73. Clarke, N. F. (2011) Congenital fiber-type disproportion. Semin Pediatr Neurol, 18, 264-271.

74. Sarnat, H. B. and Silbert, S. W. (1976) Maturational arrest of fetal muscle in neonatal myotonic dystrophy. A pathologic study of four cases. Arch Neurol, 33, 466-474.

75. Sarnat, H. B., Roth, S. I. and Jimenez, J. F. (1981) Neonatal myotubular myopathy: neuropathy and failure of postnatal maturation of fetal muscle. Can J Neurol Sci, 8, 313-320.

76. Dehkharghani, F., Sarnat, H. B., Brewster, M. A. and Roth, S. I. (1981) Congenital muscle fiber-type disproportion in Krabbe's leukodystrophy. Arch Neurol, 38, 585-587.

77. Clarke, N. F. and North, K. N. (2003) Congenital fiber type disproportion—30 years on. J Neuropathol Exp Neurol, 62, 977-989.

78. Del Bigio, M. R., Chudley, A. E., Sarnat, H. B., Campbell, C., Goobie, S., Chodirker, B. N. and Selcen, D. (2011) Infantile muscular dystrophy in Canadian aboriginals is an alphaB-crystallinopathy. Ann Neurol, 69, 866-871.

79. Clarke, N. F., Kolski, H., Dye, D. E., Lim, E., Smith, R. L., Patel, R., Fahey, M. C., Bellance, R., Romero, N. B., Johnson, E. S. et al. (2008) Mutations in TPM3 are a common cause of congenital fiber type disproportion. Ann Neurol, 63, 329-337.

80. Lawlor, M. W., Dechene, E. T., Roumm, E., Geggel, A. S., Moghadaszadeh, B. and Beggs, A. H. (2010) Mutations of tropomyosin 3 (TPM3) are common and associated with type 1 myofiber hypotrophy in congenital fiber type disproportion. Hum Mutat, 31, 176-183.

81. Munot, P., Lashley, D., Jungbluth, H., Feng, L., Pitt, M., Robb, S. A., Palace, J., Jayawant, S., Kennet, R., Beeson, D. et al. (2010) Congenital fibre type disproportion associated with mutations in the tropomyosin 3 (TPM3) gene mimicking congenital myasthenia. Neuromuscul Disord, 20, 796-800.

82. Ottenheijm, C. A., Lawlor, M. W., Stienen, G. J., Granzier, H. and Beggs, A. H. (2011) Changes in crossbridge cycling underlie muscle weakness in patients with tropomyosin 3-based myopathy. Hum Mol Genet, 20, 2015-2025.

83. Clarke, N. F., Waddell, L. B., Cooper, S. T., Perry, M., Smith, R. L., Kornberg, A. J., Muntoni, F., Lillis, S., Straub, V., Bushby, K. et al. (2010) Recessive mutations in RYR1 are a common cause of congenital fiber type disproportion. Hum Mutat, 31, E1544-1550.

84. Laing, N. G., Clarke, N. F., Dye, D. E., Liyanage, K., Walker, K. R., Kobayashi, Y., Shimakawa, S., Hagiwara, T., Ouvrier, R., Sparrow, J. C. et al. (2004) Actin mutations are one cause of congenital fibre type disproportion. Ann Neurol, 56, 689-694.

85. Sobrido, M. J., Fernandez, J. M., Fontoira, E., Perez-Sousa, C., Cabello, A., Castro, M., Teijeira, S., Alvarez, S., Mederer, S., Rivas, E. et al. (2005) Autosomal dominant congenital fibre type disproportion: a clinicopathological and imaging study of a large family. Brain, 128, 1716-1727.

86. Ortolano, S., Tarrio, R., Blanco-Arias, P., Teijeira, S., Rodriguez-Trelles, F., Garcia-Murias, M., Delague, V., Levy, N., Fernandez, J. M., Quintans, B. et al. (2011) A novel MYH7 mutation links congenital fiber type disproportion and myosin storage myopathy. Neuromuscul Disord, 21, 254-262.

87. Clarke, N. F., Kidson, W., Quijano-Roy, S., Estournet, B., Ferreiro, A., Guicheney, P., Manson, J. I., Kornberg, A. J., Shield, L. K. and North, K. N. (2006) SEPN1: associated with congenital fiber-type disproportion and insulin resistance. Ann Neurol, 59, 546-552.

88. Brandis, A., Aronica, E. and Goebel, H. H. (2008) TPM2 mutation. Neuromuscul Disord, 18, 1005.
89. Clarke, N. F., Smith, R. L., Bahlo, M. and North, K. N. (2005) A novel X-linked form of congenital fiber-type disproportion. Ann Neurol, 58, 767-772.
90. Kajino, S., Ishihara, K., Goto, K., Ishigaki, K., Noguchi, S., Nonaka, I., Osawa, M., Nishino, I. and Hayashi, Y. K. (2014) Congenital fiber type disproportion myopathy caused by LMNA mutations. J Neurol Sci, 340, 94-98.
91. Benedetti, S., Menditto, I., Degano, M., Rodolico, C., Merlini, L., D'Amico, A., Palmucci, L., Berardinelli, A., Pegoraro, E., Trevisan, C. P. et al. (2007) Phenotypic clustering of lamin A/C mutations in neuromuscular patients. Neurology, 69, 1285-1292.
92. Wei, L. and Dirksen, R. T. (2010) Ryanodinopathies: Ryr-Linked Muscle Diseases. Current Topics in Membranes, 66, 139-167.

EXAMPLES

Small Molecule Screening in Ryanodine Receptor Mutant Zebrafish for Therapeutic Development in Core Myopathy Introduction Human cells express three distinct isoforms of the ryanodine receptor, each encoded by a different gene: RyR1, RyR2, and RyR3[1,2]. RyR1 and RyR2 are predominantly expressed in skeletal and cardiac muscles, respectively, whereas RyR3 has widespread expression during development but is present at relatively low levels. The skeletal muscle RYR1 gene encodes a large, homotetrameric transmembrane ion channel that serves as one of the major intracellular calcium channels in this tissue[3]. First identified in the 1980s and named for its ability to bind the plant alkaloid ryanodine, RyR1 resides on the terminal sarcoplasmic reticulum (SR) and exists in close proximity with the T-tubule[4]. Its functional role is to mediate excitation-contraction coupling, by releasing calcium from the SR into the cytosol in response to motor neuron stimulation at the neuromuscular junction.

Causative mutations in RYR1 are associated with a wide range of pathologies. Inherited as a dominant trait, RYR1 mutations often give rise to malignant hyperthermia (MH) and/or central core disease (CCD). MH is a pharmacogenetic condition manifesting as muscle rigidity and a dramatic rise in body temperature upon exposure to certain anesthetics or environmental conditions[3,5,6], whereas CCD is characterized by infantile hypotonia and weakness affecting proximal muscles. Pathologically, the cardinal diagnostic feature of patients with CCD is the presence of "central cores" running along the long axis of myofibers that are devoid of mitochondria and deficient in oxidative enzymes, phosphorylase activity, and glycogen. Only occasionally will autosomal recessive RYR1 mutations yield CCD pathology. More frequently, recessive mutations will lead to alternative findings on muscle biopsy, including characteristic features of multiminicore disease (MmD)[7], centronuclear and core-rod myopathies[8,9], congenital fiber type disproportion[10,11], and muscular dystrophy[12].

The molecular mechanisms underlying RYR1-related disorders are not yet precisely defined, although trends regarding some genotype-phenotype correlations are emerging. Vis-à-vis the functional effects of dominant RYR1 mutations, MH is believed to arise from "hyperactive" RYR1 channels that show increased sensitivity to RyR1 agonists in vitro. Caffeine and halothane both activate RyR1 channels carrying MH mutations at lower concentrations than those required to stimulate $Ca^{2+}$ release in normal channels[13-15]. RyR1 dysfunction in CCD is debated between two models: increased cytosolic calcium levels and depletion of SR calcium stores ("leaky channel" hypothesis) and disruptions in excitation-contraction coupling ("uncoupling" hypothesis)[15-17]. In vitro studies have demonstrated reduced levels of stimulated calcium release consistent with both hypotheses[14,17-21]. The functional consequences of recessive RYR1 mutations, however, have only begun to be elucidated, though poorly functioning and reduced numbers of RyR1 channels are a common finding[22]. Protein levels of RyR1 and the physically coupled dihydropyridine receptor (DHPR) are both reduced in autosomal recessive RYR1 patient muscles[23]. Localization of the DHPR alpha subunit is also perturbed in cultured myotubes treated with RYR1-targeting siRNAs[23]. These two alterations result in impaired excitation-contraction coupling[23]. Recessive RYR1 mutations have also been tied to changes in cellular secretion of interleukin 6[17,24]. This cytokine's involvement in a variety of biological events across many tissues and cell types highlights the importance of identifying new molecular pathways that might be involved in RYR1 disease pathogenesis.

Several vertebrate models have been created to help define the histopathological course of various RYR1-related disorders. Heterozygous mice carrying the p.R163C and p.Y522S mutations undergo full MH episodes when exposed to volatile anesthetics or heat[25,26]. Their skeletal muscles display caffeine- and heat-induced contractures in vitro, as well as increased calcium release from leaky RyR1 channels under conditions of oxidative stress[26,27]. Another established murine model is the heterozygous line carrying the p.I4895T uncoupling mutation at the C-terminus of RYR1. These mice exhibit a slowly progressive myopathy and age-dependent formation of cores and nemaline rods in skeletal muscles[28]. There are currently no working mouse models of recessive RYR1-related myopathies, since homozygous Ryr1$^{-/-}$ mice die perinatally with skeletal muscles unresponsive to electrical stimulation[29]. Fortuitously, a spontaneous zebrafish mutant that closely mimics human MmD has opened new doors for the study of these diseases in vivo.

The relatively relaxed (ryr1b) zebrafish mutant is homozygous for a recessive nonsense mutation in the ryr1b gene, which results in reduced levels of Ryr1 protein[30]. Whereas wild-type zebrafish larvae swim away in response to tactile stimulation, ryr1b mutants swim slowly due to weak muscle contractions despite normal output from the central nervous system. Ryr1b mutants exhibit small amorphous cores in myofibers, similar to both human MmD patients and our sepn1 zebrafish model described in the previous chapter. Furthermore, Ca2+ transients in ryr1b mutants are also drastically reduced, consistent with the prevailing hypothesis that RYR1-related disorders are chiefly due to impairments in excitation-contraction coupling.

Following initial characterization of the ryr1b zebrafish, comparative microarray expression analysis was performed on RNA isolated from mutants and wild-type clutchmates in order to identify novel pathogenic pathways associated with the loss of Ryr1 function. Several of the mis-expressed transcripts were involved in redox and cellular homeostasis[31]. This finding was particularly noteworthy since the redox regulation of RyR1's cytosolic thiol groups is known to affect the channel's gating properties, its opening in response to ions and caffeine, as well as its ability to bind calstabin and calmodulin (two proteins that help dictate RyR1-mediated Ca2+ release in skeletal muscle)[32-34]. A candidate compound approach confirmed a role for oxidative stress in these disorders when the antioxidant N-acetylcysteine was shown to ameliorate select aspects of the ryr1b phenotype, including major histopathological abnormalities[31]. In an attempt to better understand RYR1-related pathophysiology and elucidate new molecular pathways that might contribute to disease phenotypes, a chemical screen aimed at identifying lead compounds that can rescue the function of skeletal muscle in the relatively relaxed zebrafish was performed.

Materials and Methods:

Zebrafish Lines and Husbandry

Zebrafish (*Danio rerio*) were bred and maintained under standard conditions[35]. Zebrafish (*Danio rerio*) from the wild-type Oregon AB line were bred and maintained according to standard procedures in the Boston Children's Hospital Aquatic Research Program facility[35]. Embryos were collected by natural spawning, staged by hours (hpf) or days (dpf) post fertilization[36], and raised at 28.5° C. in egg water. The relatively relaxed (abbreviated ryr1b) line was acquired after its full characterization as a zebrafish model of MmD[30]. The skeletal muscle phenotype in homozygous ryr1b mutants is transmitted in a recessive manner such that 25% of the offspring from mating heterozygous ryr1b$^{+/-}$ adults show diminished touch-evoked swimming by 5 dpf. Embryos were staged by hours (hpf) or days (dpf) post fertilization at 28.5° C.[36]. All animal work was performed with approval from the Boston Children's Hospital Animal Care and Use Committee (14-05-2717R).

Chemical Library

The Prestwick2 chemical library was supplied by the Institute of Chemistry and Cell Biology Screening Facility at Harvard Medical School and used as the source of small molecules for chemical screening experiments. This library contains 1,120 small molecule composed of 90% marketed drugs and 10% bioactive alkaloids or related substances. Compounds in the Prestwick2 collection were selected for their high chemical and pharmacological diversity, as well as their established bioavailability and safety in humans[37].

Chemical Screening

Primary screen. For the primary screen, twenty embryos (1 dpf) resulting from a mating of heterozygous ryr1b zebrafish were manually sorted into 48-well plates containing 250 μL embryo 1×E3 medium (5.0 mM NaCl, 0.17 mM KCl, 0.33 mM CaCl$_2$*2H$_2$O, 0.33 mM MgSO$_4$*7H$_2$O) and four pooled chemicals from the Prestwick2 chemical library. Each chemical pool was assayed in duplicate using embryos from two independent clutches, for a total of 24 distinct pools tested per plate (FIG. 1). The chemicals were dissolved to a final concentration of 2.0 μg/mL and 0.4% DMSO, which is similar to concentrations other groups have used in zebrafish studies[37,38]. As a negative control, twenty embryos from each clutch were cultured without chemicals in vehicle only (0.4% DMSO) (FIG. 1). Larvae obtained from wild-type (Oregon AB) matings served as positive controls in separate plates. All plates containing embryos were incubated at 28.5° C. and maintained as initially treated for 5 days. Dead embryos were removed from wells when observed during the first 4 days of the study. On day 5, dead or "motion-dead" larvae were scored alongside living larvae.

Figures 2A, 2B:
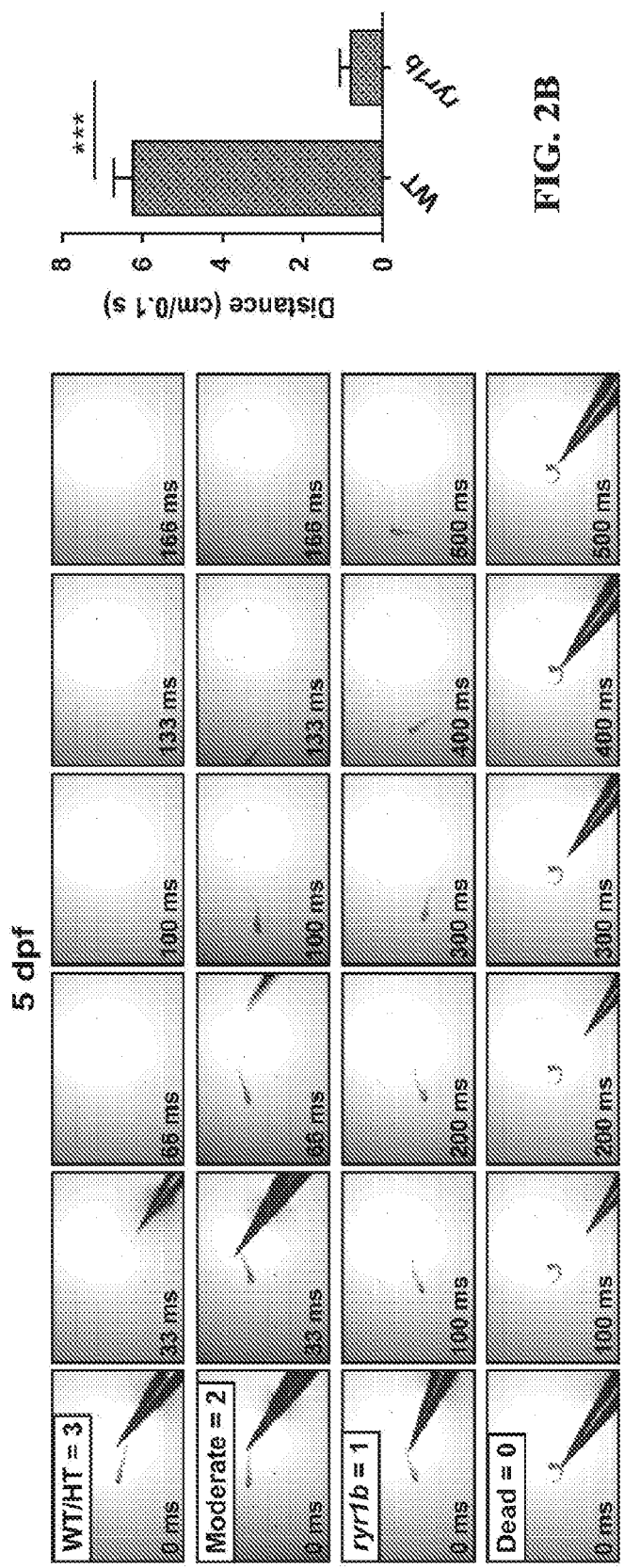
FIGS. 2A-2B show the numerical scoring of touch-evoked escape behaviors.

At 5 dpf, pools were scored for their ability to improve the survival and touch-evoked escape behaviors of ryr1b homozygous mutants using the following numeric scoring system: 3=4-6 cm, fast (wild-type); 2=2-4 cm (moderate); 1=<2 cm, slow (ryr1b); 0=no movement (dead) (FIG. 2A). Survival, swimming, and combined endpoints of the primary screen were then examined for their ability to distinguish positive from negative controls. Since the survival component of the primary screen proved to be most statistically robust (Z'-factor$_{survival}$=1−[(3*($\sigma_p$+$\sigma_n$))/|$\mu_p$−$\mu_n$|]= 0.60), chemical pools with significantly higher ryr1b survival rates than DMSO-treated controls were considered hits (P<0.005). Taking into account both experimental replicates (n=40), hit pools contained at least 37 alive larvae on day 5 (i.e., 70-100% of the larvae assumed to be ryr1b mutants survived the duration of the study), and were selected for analysis in a secondary screen.

Secondary Screen.

In the secondary screen, hit pools were separated and tested as 68 individual chemicals. Screening was performed precisely as described for the primary screen with few modifications. Embryos were raised in wells containing 750 μL 1×E3 medium, as opposed to 250 μL, although the final concentration of each compound was maintained at 2.0 μg/mL. Additionally, because full establishment of our heterozygous ryr1b line resulted in improved robustness of a combined survival and mobility assay, ryr1b larvae in this tier of the screen were evaluated in terms of an overall "vitality" score (Z'-factor=0.37). Vitality scores, weighting survival and swimming ratios appropriately, were calculated as (#Dead*0)+(#ryr1b*1)+(#Moderate*2)+(#Wild-type*3). Theoretical maximum and minimum scores were 60 and 0, respectively, with an expected score of 50 in DMSO-treated controls. Secondary screen hits (P<0.05), considered "candidate" compounds, are currently being examined in dose-response and long-term studies.

Genotyping of ryr1b Mutants

The relatively relaxed zebrafish was initially identified due to a spontaneous autosomal recessive mutation within the ryr1b gene[30]. Specifically, ryr1b mutants carry a 4046 base pair (bp) DNA insertion in the intron between exons 48 and 49 that includes an additional 32 bp sequence found in mutant cDNA (FIG. 3)[30]. Genotypes of individual embryos were examined using three-primer genomic PCR, with an expected wild-type band of 1,668 bp and a mutant band of 653 bp. Primer sequences were as follows: ryr1b #1 (forward): 5'-GTGGGTTTCTTGCCCGATAT-GAGAGCTTCA-3' (SEQ ID NO: 4); ryr1b #2 (reverse): 5'-AACAGTGGGGCACATTTAGTGAGCAGAGG-3' (SEQ ID NO: 5); and ryr1b #3 (reverse): 5'-CTT-TAAATAAGCTCTGTGGCATTGGTTGACTC-3' (SEQ ID NO: 6).

Western Blotting

Western blotting was performed on groups of 50-100 wild-type or mutant zebrafish larvae at 5 dpf. Mouse monoclonal anti-phospho-STAT3 (1:1000, D128-3, MBL International, Woburn, Mass., USA) and mouse monoclonal anti-β-actin (1:1000, A5441, Sigma) were used as primary antibodies, and were visualized with HRP-conjugated anti-rabbit (1:2500, 170-6515) and anti-mouse (1:5000, 170-6516) IgG (BioRad). Of three candidates, a reliable antibody for the detection of total Stat3 in zebrafish was not found. Phospho-Stat3 band intensities were normalized to control bands and quantified in Image J (NIH).

Real-Time PCR (RT-PCR)

Total RNA was prepared from zebrafish embryos using RNeasy fibrous tissue mini kits (Qiagen). cDNAs were synthesized from 1-2 μg of total RNA using Superscript III reverse transcriptase (Invitrogen) and random hexamers. To assess relative stat3 expression levels in 5 dpf embryos, quantitative real-time RT-PCR amplification of cDNAs was performed with a Taqman assay for stat3 exon15-exon16 (Applied Biosystems) on a 7300 Real Time PCR System (Applied Biosystems). Gapdh served as the control to normalize stat3 expression using the $2^{-\Delta\Delta Ct}$ method.

Activity Monitoring

Zebrafish behavioral parameters were defined using the Noldus Daniovision activity monitoring system. In 12-well plates, wild-type and mutant larvae (5 or 20 dpf) were placed into the machine with the light box off. After a 10 min acclimation to the dark, larvae were stimulated by light exposure for 50 min. This cycle was repeated two times during the course of a single trial. Swimming behaviors were recorded over the entire 2.0-hour period with an infrared light source. Three independent trials were performed with larvae from three different clutches, examining a total of 14-20 wild-type and ryr1b larvae from both DMSO- and nifuroxazide-treated groups. Behavioral parameters recorded include frequency, mean velocity, total distance, and cumulative duration of movement, and reflect the average of all larvae in an experimental group.

Calcium Imaging in Murine Cell Culture

Primary myoblasts from C57BL/6N mice were isolated and differentiated as described previously[39]. Calcium imaging was performed 5 days after differentiation in myotubes loaded with 3 μM Fluo-4-AM (Life Technologies). Myotubes were imaged in imaging buffer (125 mM NaCl, 5 mM KCl, 2 mM $CaCl_2$, 1.2 mM $MgSO_4$, 6 mM glucose, 2 mM $Ca^{2+}$, 25 mM Hepes/Tris, pH 7.4) at 490-500 nm with a Stanford Photonics 10 bit digital intensified CCD using a DG4 multi-wavelength light source. Fluorescent emission at 510 was acquired and analyzed using QED Imaging software (QED Software, Pittsburgh, Pa., USA) from regions of interest within each myotube at 30 frames per second. Sensitivity to $K^+$-depolarization and caffeine-activation were determined by a 5 second perfusion with 5-6 volumes of KCl (10 mM to 60 mM) or caffeine (3 mM to 40 mM).

Statistical Analysis

GraphPad Prism 7 software (GraphPad Software Inc.) was used to graph all quantitative data and perform statistical analyses. P values for pairwise comparisons were determined using a two-tailed Student's t-test. P values for Kaplan-Meier survival curves were calculated using a log-rank test, and for dose response curves in murine myotubes using an extra sum-of-squares F test. Multiple comparison tests were calculated using one-way ANOVAs, followed by Tukey's honestly significant difference (USD) post hoc tests (alpha=0.05). Studies were considered significant when $P<0.05$ (*), $P<0.01$ (), and $P<0.001$ (*). All quantitative data are shown as the mean±standard deviation.

Example 1. Primary Screening of Ryr1b Zebrafish

Figure 4:
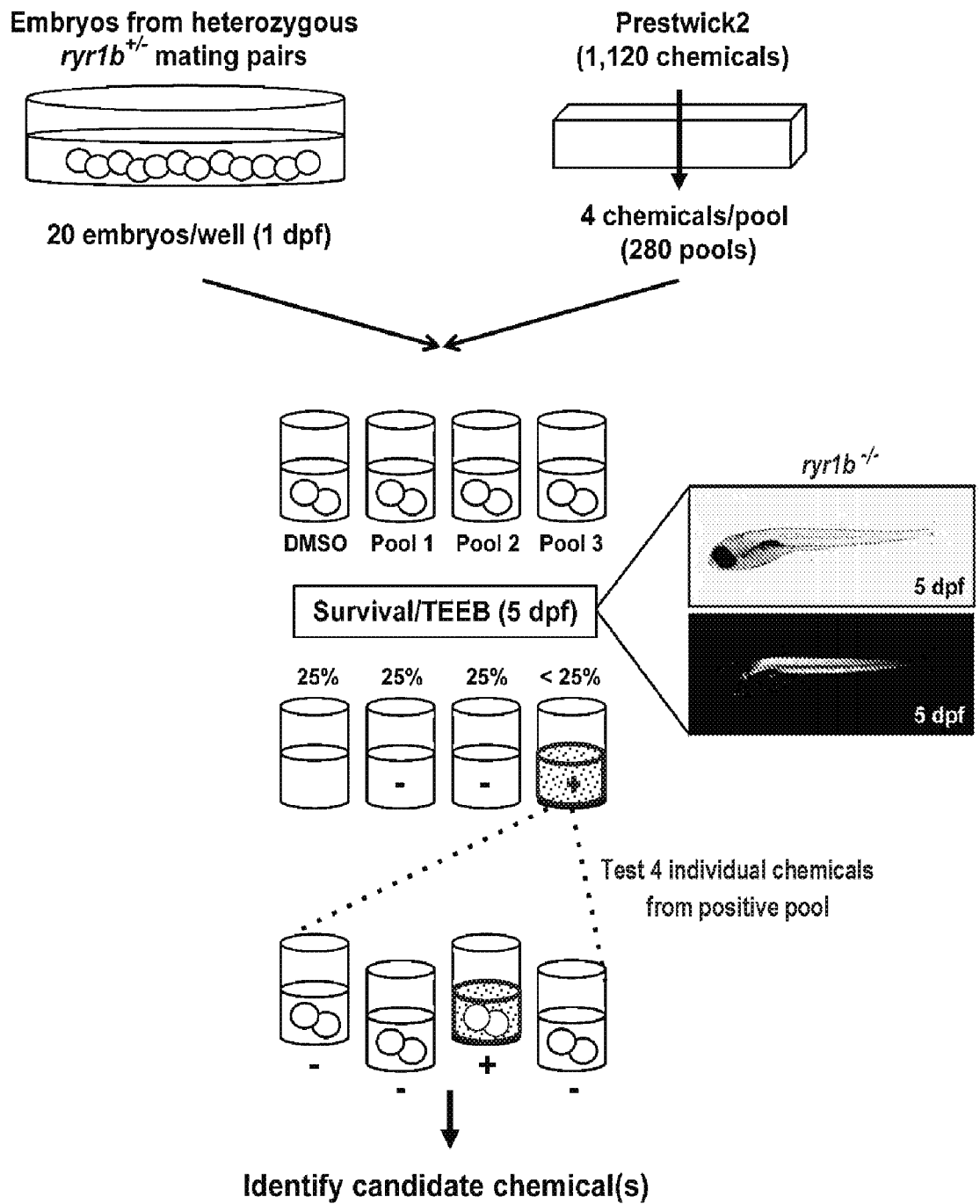
FIG. 4 is a schematic outline of a two-tiered ryr1b chemical screen. Primary and secondary ryr1b chemical screening procedures were performed on compounds from the Prestwick2 chemical library. Images of homozygous ryr1b mutants at 5 dpf under brightfield (top) and polarized light (bottom) are also included, illustrating that mutants exhibit wild-type birefringence levels and must therefore be assayed for a skeletal muscle phenotype using an alternative assay, touch-evoked escape behavior (TEEB).
Figure 5:
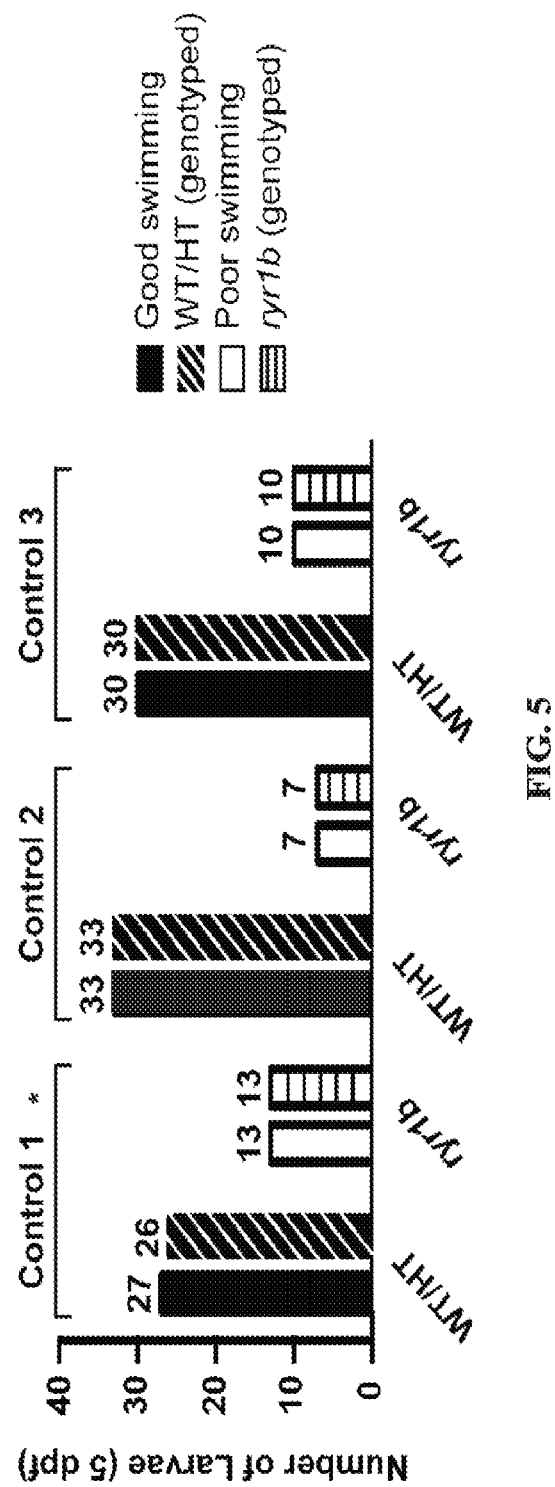
FIG. 5 shows screened wells containing an expected 3:1 ratio of unaffected (WT) to affected (ryr1b) larvae. Genotypes and phenotypes compared in three independent DMSO-treated controls verify approximate 3:1 ratio of wild-type/heterozygous larvae to ryr1b mutant larvae. Each group represents the contents of two wells, considered experimental replicates (n=40). Note: Genotyping of one larva in "Control 1" was not conclusive (*).
Figure 6:
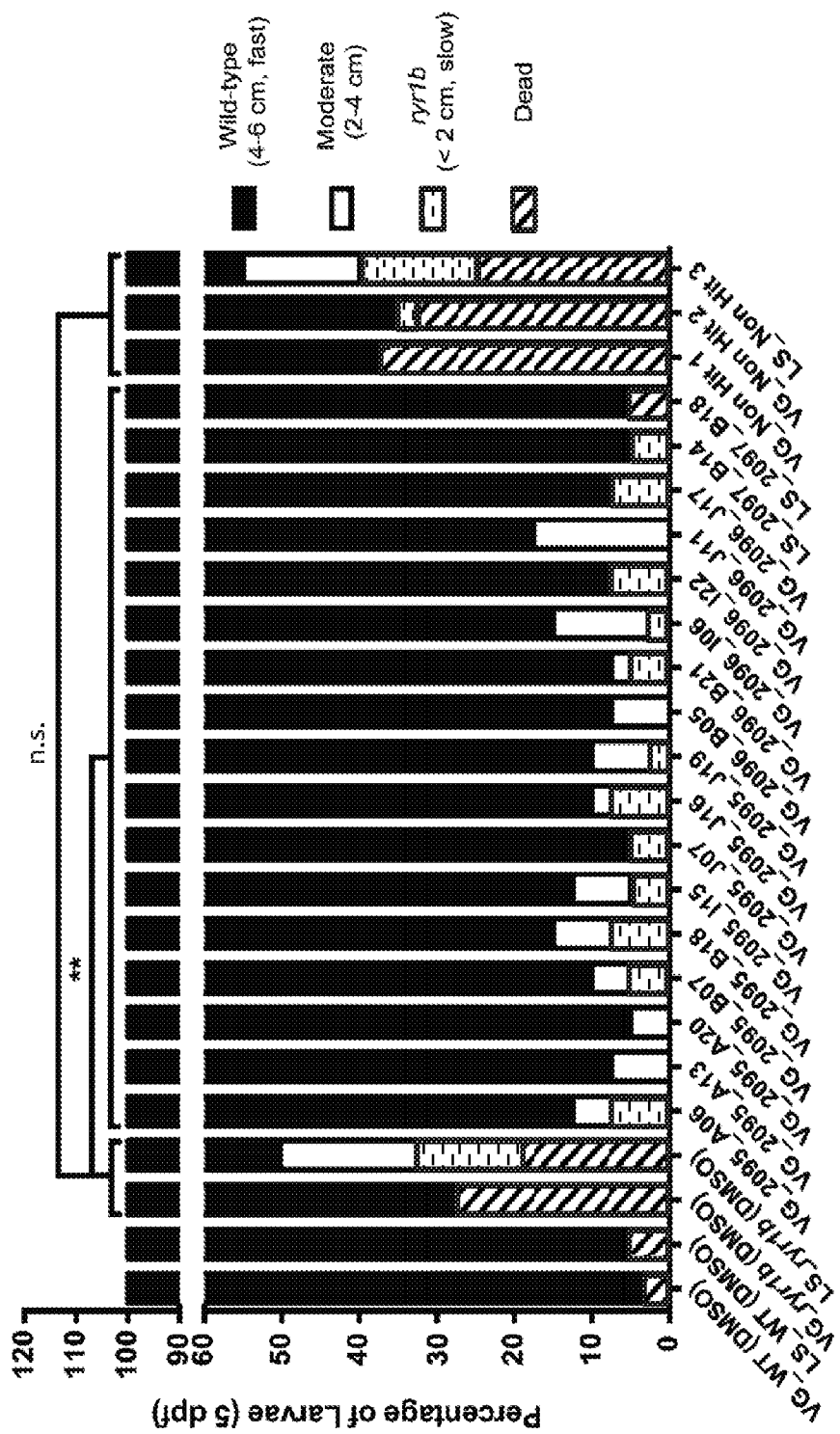
FIG. 6 shows mobility and survival measurements of the primary screen "hit" pools. All treatments were performed in duplicate, with each replicate consisting of 20 larvae from heterozygous ryr1b matings (n=40). Larvae obtained from wild-type zebrafish (strain AB) matings served as positive controls. Significance was determined by pairwise comparisons between experimental and control pools using a Student's t-test. "LS" and "VG" designates the person who performed each trial, as two individuals conducted the ryr1b primary screen over the course of two years (Green=Wild type; Yellow=Moderate; Orange=ryr1b; Red=Dead).

Homozygous ryr1b mutants do not have morphological or birefringence abnormalities during the first week of development, and are typically only distinguishable from wild-type and heterozygous clutchmates by touch-evoked swimming behaviors (FIG. 2B). However, mutants obtained from newly established ryr1b[+/−] lines also exhibit increased mortality and die before 5 dpf, prioritizing survival as the most robust endpoint for chemical screening. Therefore, for the primary screen (schematically outlined in FIG. 4), 280 chemical pools from a total of 1,120 chemicals in the Prestwick2 chemical library were tested for their ability to improve the survival rate of homozygous ryr1b mutants. Of these chemical pools, 41 (14.6%) resulted in the death of all embryos, whereas the remaining 239 yielded surviving larvae after four full days of treatment (Table 1). Surviving wells were expected, and subsequently confirmed, to contain approximately 25% homozygous ryr1b mutants (FIG. 5). Assuming this ratio, the 17 chemical pools found to significantly improve ryr1b mutant survival compared to DMSO-treated controls were considered hits ($P<0.005$) and selected for analysis in a secondary screen (FIG. 6).

TABLE 1

Embryonic zebrafish survival in Prestwick2 library chemical screen.

|  | Total | Viable | Lethal |
|---|---|---|---|
| Survival in Primary Screen |  |  |  |
| Chemical Pools | 280 | 239 | 41 |
| Chemicals | 1,120 | 956 | 164 |
| Percentage | 100.0 | 85.4 | 14.6 |
| Survival in Secondary Screen |  |  |  |
| Chemicals | 68 | 58 | 10 |
| Percentage | 100.0 | 85.3 | 14.7 |

Example 2. Secondary Screening of Ryr1b Zebrafish

Figure 7:
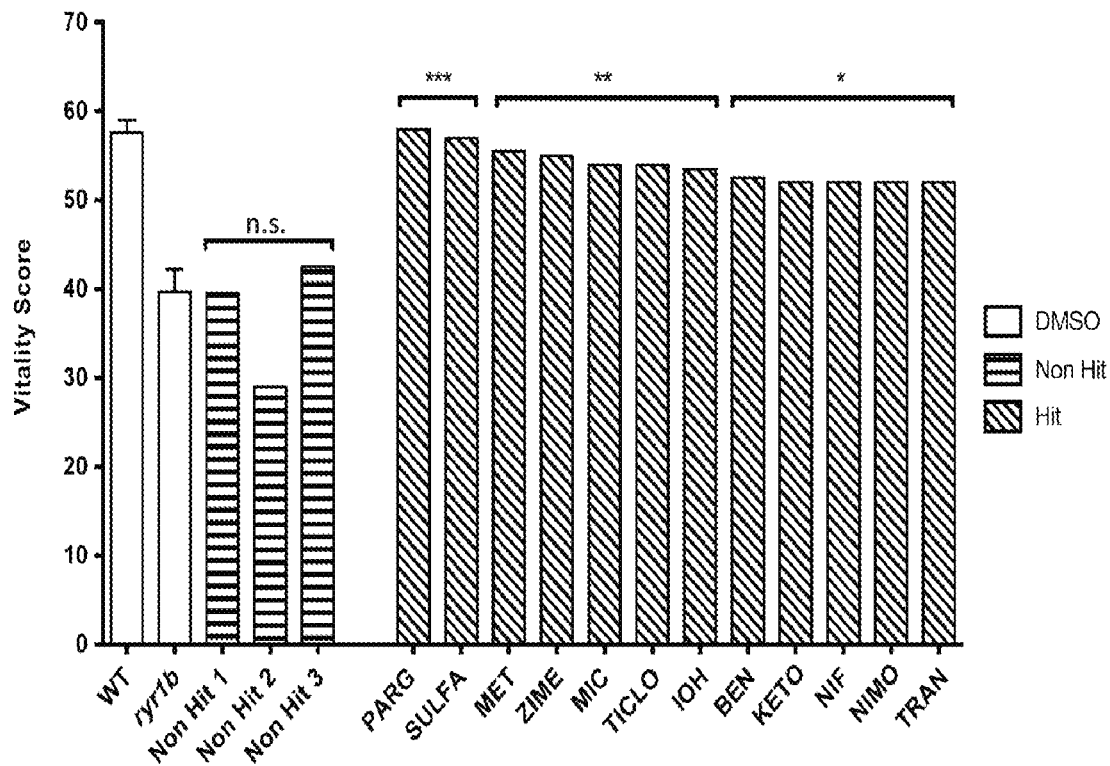
FIG. 7 shows the vitality scores of individual "hit" compounds on secondary screens. Each scored compound represents an average of two replicates, consisting of 20 larvae from heterozygous ryr1b matings (n=40). Larvae obtained from wild-type AB matings served as positive controls. Experimental treatments that significantly improved ryr1b mutant survival and mobility (combined as "vitality") compared to DMSO-treated controls were considered candidate "hit" compounds warranting further study. Significance was determined by pairwise comparisons between control and experimental pools using a Student's t-test. Vitality score=(#Dead*0)+(#ryr1b*1)+(#Moderate*2)+(#Wild-type*3). Standard deviations shown for positive and negative controls were calculated based on results from 5 and 21 independent experiments, respectively.

The second tier of the chemical screen was performed two years following the primary screen, with a fully established ryr1b[+/−] line. Healthier clutches tended to result in better survival of homozygous ryr1b mutants. Median mutant life spans more accurately adhered to the 7-15 day estimate previously published[30]. Therefore, in the secondary screen, hit chemical pools were separated into individual compounds and each of 68 total compounds was examined for its ability to positively influence both ryr1b survival and motor function (referred to in combination as "vitality"). Weighing survival and swimming appropriately, twelve compounds were found to improve ryr1b mutant vitality compared to DMSO-treated controls (Table 2; FIG. 7). While these twelve compounds varied with regard to annotated function, several showed considerable overlap. These included two anti-inflammatory agents (sulfasalazine and ketoprofen), two monoamine oxidase inhibitors (pargyline hydrochloride and tranylcypromine hydrochloride), and two ion channel modulators (metolazone and nimodipine).

TABLE 2

Candidate compounds identified by two-tiered ryr1b chemical screen.

| Vitality Score | Chemical Name | Formula | MW | Mechanism of Action |
|---|---|---|---|---|
| 58.0 | Pargyline hydrochloride * | $C_{11}H_{14}ClN$ | 195.69 | Irreversible monoamine oxidase (MAO) inhibitor |
| 57.0 | Sulfasalazine | $C_{18}H_{14}N_4O_5S$ | 398.39 | NF-KB inhibitor; anti-inflammatory |
| 55.5 | Metolazone ** | $C_{16}H_{16}ClN_3O_3S$ | 365.83 | Sodium-chloride channel inhibitor |
| 55.0 | Zimelidine dihydrochloride monohydrate ** | $C_{16}H_{21}BrCl_2N_2O$ | 408.16 | Selective serotonin reuptake inhibitor |

TABLE 2-continued

Candidate compounds identified by two-tiered ryr1b chemical screen.

| Vitality Score | Chemical Name | Formula | MW | Mechanism of Action |
|---|---|---|---|---|
| 54.0 | Miconazole *** | $C_{18}H_{14}Cl_4N_2O$ | 416.13 | Anti-fungal agent |
| 54.0 | Ticlopidine hydrochloride *** | $C_{14}H_{15}Cl_2NS$ | 300.25 | Inhibitor of platelet aggregation |
| 53.5 | Iohexol | $C_{19}H_{26}I_3N_3O_9$ | 821.14 | Low-osmolality contrast agent |
| 52.5 | Benoxinate hydrochloride *** | $C_{17}H_{29}ClN_2O_3$ | 344.88 | Surface anaesthetic |
| 52.0 | Ketoprofen | $C_{16}H_{14}O_3$ | 254.28 | Cyclooxygenase inhibitor; anti-inflammatory |
| 52.0 | Nifuroxazide | $C_{12}H_9N_3O_5$ | 275.22 | JAK/STAT signaling inhibitor |
| 52.0 | Nimodipine | $C_{21}H_{26}N_2O_7$ | 418.44 | Dihydropyridine calcium channel blocker |
| 52.0 | Tranylcypromine hydrochloride * | $C_9H_{12}ClN$ | 169.65 | Irreversible MAO inhibitor |

Asterisks indicate compounds originating from the same chemical pool.
MW, molecular weight.

Figures 8A, 8B:
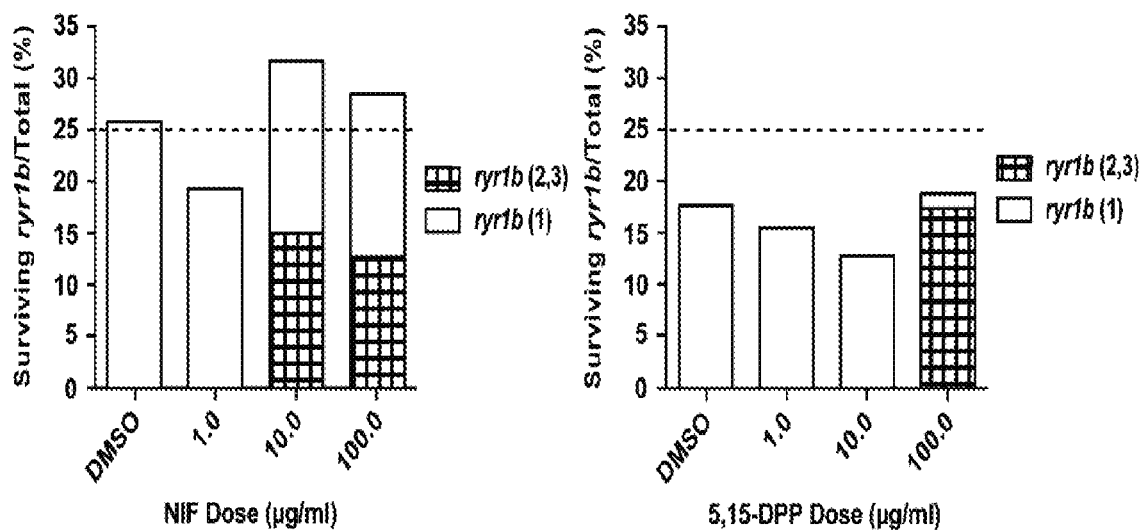

Example 3. Dose-Response Identifies Nifuroxazide as a Modulator of the Ryr1b Phenotype The primary and secondary screens only tested chemical pools and individual compounds at a single concentration (2.0 µg/mL). Although beneficial in a high-throughput context, this approach can result in false positives and false negatives. All twelve candidate compounds are now being investigated to identify those that exhibit a dose-dependent, positive effect on the ryr1b mutant phenotype. Nifuroxazide (NIF), a potent inhibitor of the JAK-STAT signaling pathway, was one of the first candidates found to improve ryr1b mobility in a dose-dependent manner (FIG. 8A). For analysis, pools of 20 larvae obtained from heterozygous ryr1b matings were treated in duplicate with DMSO or with one of three different concentrations of NIF (1.0-100.0 µg/mL) at 1 dpf and scored for touch-evoked escape behaviors at 5 dpf. All scored larvae were then genotyped using three-primer genomic PCR. An intermediate dose of 10 µg/mL resulted in confirmed ryr1b larvae that swam similar to wild-type controls. Next, hit expansion was used to verify JAK-STAT as a potential molecular pathway involved in ryr1b mutant pathology. Whereas NIF acts by reducing tyrosine phosphorylation of JAK2 kinase and blocking downstream phosphorylation of the transcription factor STAT3, 5,15-diphenylporphyrin (5,15-DPP) is a cell permeable porphyrin that specifically inhibits interleukin 6-induced STAT3 activation by preventing its dimerization. As anticipated, 5,15-DPP also showed a dose-response relationship with ryr1b mutants and exhibited optimal activity at 100.0 µg/mL (FIG. 8B). A higher effective dose for 5,15-DPP was consistent with the $IC_{50}$ measurements reported for each compound[40,41].

In skeletal muscle, activation of the JAK-STAT pathway is correlated with myogenic differentiation, and inhibition of JAK-STAT signaling in dystrophic mice has been shown to rescue defects in muscle regeneration[42-44]. To determine whether zebrafish stat3 is differentially expressed in the wild-type and Ryr1-deficient background, quantitative real-time RT-PCR was performed using fluorescently tagged Taqman probes. Interestingly, stat3 expression is significantly increased in ryr1b mutants in comparison with unaffected controls at 5 dpf (FIG. 8C). Western blots subsequently showed that zebrafish with homozygous ryr1b mutations are also more sensitive to pharmacological inhibition of Stat3. Levels of phosphorylated Stat3 protein experienced a larger decrease in ryr1b mutants than in unaffected controls following NIF treatment (10 µg/mL) (FIG. 8D).

Example 4. Nifuroxazide Improves Contractile Forces in Ryr1-Deficient Larvae Ryr1b mutants display weaker muscle contractions than wild-type clutchmates as early as 2 dpf[30]. To investigate whether NW affects contractile strength in zebrafish, ryr1b mutants and unaffected controls were treated with the compound for several days. At 5 dpf, electrophysiological studies were performed with the help of Dr. Jeffrey Widrick. Whereas ryr1b mutants exhibited reduced tetanic force per cross-sectional area compared to unaffected controls, tetanic forces in NIF-treated mutants were restored to wild-type levels (FIG. 9A). These data, together with published observations that $Ca^{2+}$ transients are smaller in Ryr1-deficient zebrafish and mouse muscles relative to wild-type, prompted the hypothesis that nifuroxazide may act, either directly or indirectly, on defective excitation-contraction coupling in ryr1b mutants.

Depolarization of the muscle membrane causes a transient increase in cytoplasmic $Ca^{2+}$, a result of excitation-contraction coupling that leads to actin-myosin sliding and skeletal muscle contraction[45]. To examine the effect of NIF on $Ca^{2+}$ transients in vertebrate muscle, wild-type murine myotubes were cultured in the presence or absence of compound for 5 days. Depolarization-induced calcium release was then studied in response to increasing doses of caffeine. As expected, only very modest increases in calcium release were observed in the wild-type background (FIG. 9B). While these data are supportive of an effect of the compound on RyR1-mediated calcium release, more experiments are necessary and must be designed to look at other aspects of calcium homeostasis in RyR1 deficiency, such as SR calcium load, resting free calcium concentration, and/or passive calcium entry. This particular experiment was not possible in RYR1 null muscle cells since these do not respond to any direct agonist of this channel (e.g., caffeine, potassium).

Figure 10A:
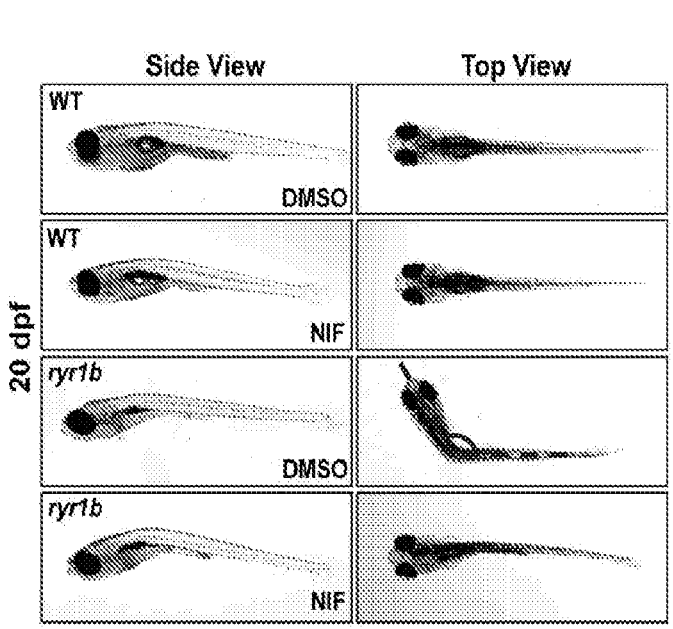
FIGS. 10A-10D show that nifuroxazide corrects ryr1b morphological features and swimming behaviors.
Figure 10D:
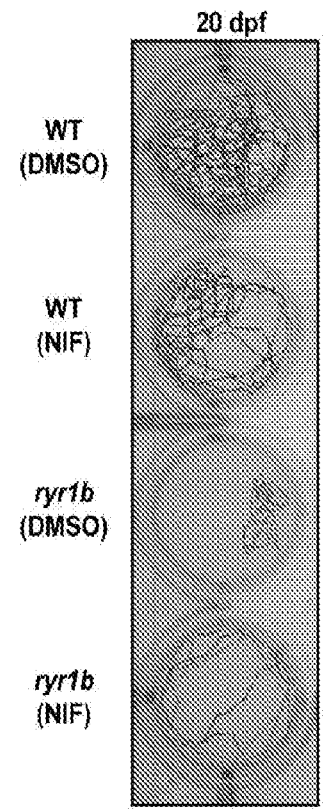
Figure 10B:
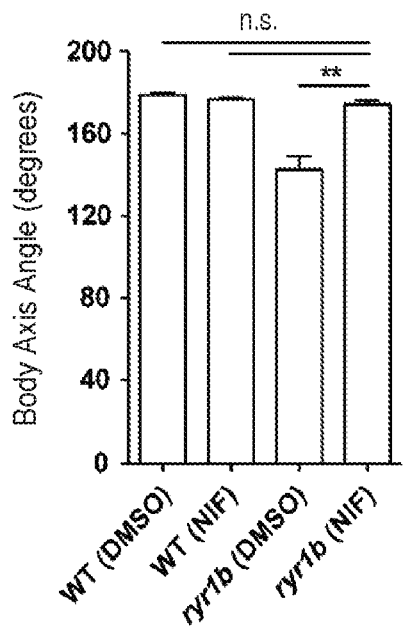

Example 5. Long-Term Stat3 Inhibition as a Potential Treatment for Homozygous Ryr1b Zebrafish Wild-type zebrafish larvae display straight bodies throughout the first 20 days of life, with angles that do not deviate significantly from 180 degrees. Although homozygous ryr1b mutants do not exhibit early morphological defects, ryr1b trunks are frequently bent by 20 dpf with angles reduced to 140 degrees. This bending is likely a consequence of skeletal muscle weakness, and may be analogous to neck and trunk flexor weakness observed in human patients with MmD (FIG. 10A). To determine if NIF could correct this abnormality, larvae were treated with the compound from 1 to 20 dpf. After 20 days, body angles were measured as the angle of intersection between two lines, one drawn between the eyes of each larva and one drawn along the trunk midline. Body angles of NIF-treated ryr1b mutants were significantly increased and statistically indistinguishable from unaffected controls (FIG. 10B). These improvements in morphology reflect long-term strengthening of ryr1b skeletal muscles as a result of exposure to NIF.

Figure 10C:
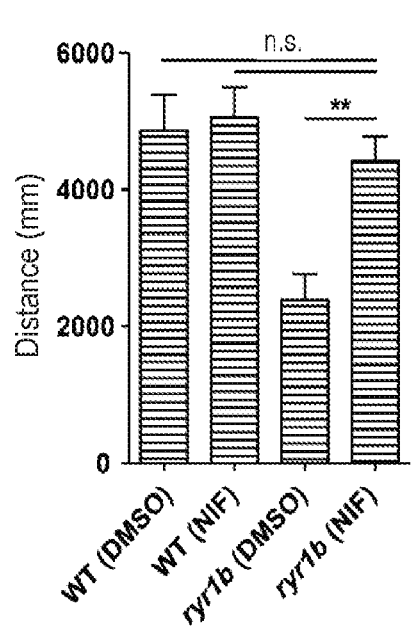

Next, to determine if long-term NIF treatment affects ryr1b motor functions, spontaneous swimming behaviors of 20 dpf larvae were quantified using the Noldus Daniovision. As expected, untreated ryr1b mutants moved significantly less than control clutchmates. In contrast, NIF treatment resulted in a large and robust increase on the distance travelled by ryr1b zebrafish, restoring their movements to the levels of NIF-treated controls (FIGS. 10C-10D). Together with the dose-response data, these findings indicate that NIF improves the motor phenotype and endurance of ryr1b mutants.

Figure 11:
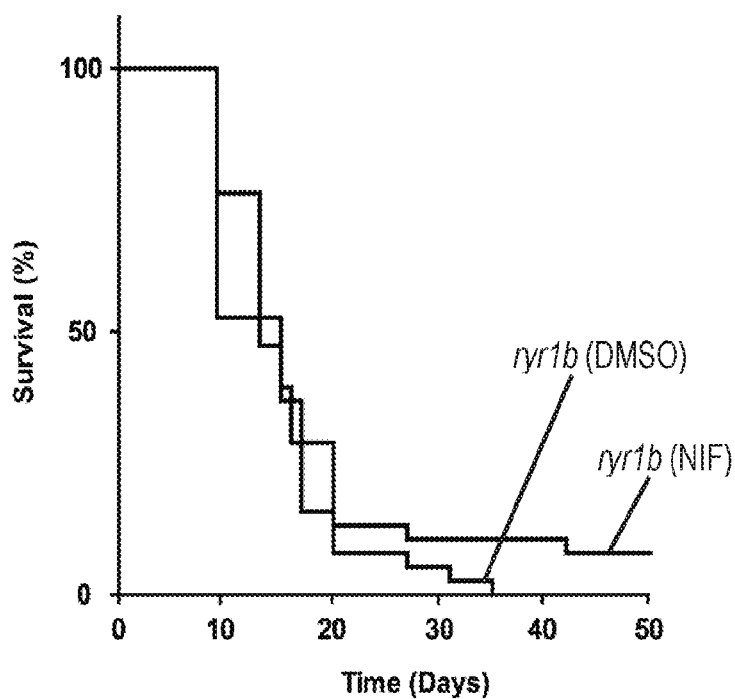
FIG. 11 shows the effect of nifuroxazide on life span of ryr1b mutants. Kaplan-Meier survival curves of ryr1b mutants treated with either DMSO or NIF (10 μg/mL) from 1 to 50 dpf. Mutants were sorted from unaffected controls at 5 dpf using a touch-evoked escape behavior assay. Untreated fish all died by 35 days of life. Median survival of DMSO-versus NIF-treated mutants was 15.0 and 13.0 days, respectively. No statistically significant differences were detected according to a log-rank test (P=0.5), however, two affected fish treated with NIF survived until termination of the study at 50 days of age.

In addition to their muscular defects, ryr1b mutants die prematurely[30]. To examine whether long-term treatment with NIF positively impacts the life span of ryr1b mutants, affected larvae (selected at 5 dpf by touch-evoked escape behavior assay) were treated with compound from 1 to 50 dpf. Despite drug-mediated improvements in anatomy and swimming, Kaplan-Meier survival curves and median survival did not significantly differ between NIF- and DMSO-treated ryr1b larvae, although select ryr1b mutants treated with NIF did survive the complete duration of the study (FIG. 11).

Figure 12A:
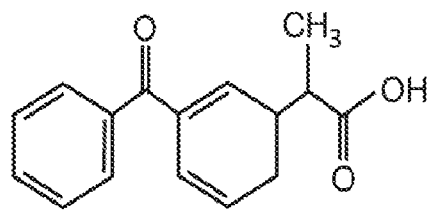
FIGS. 12A-12C show a ketoprofen dose-response and proposed mechanistic link.
Figure 12A:
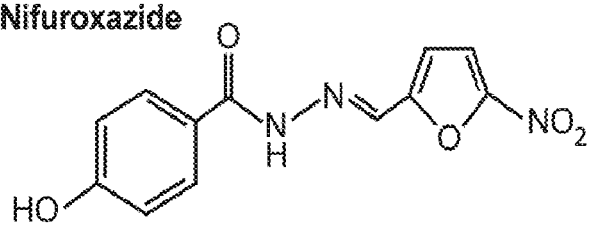
Figure 12B:
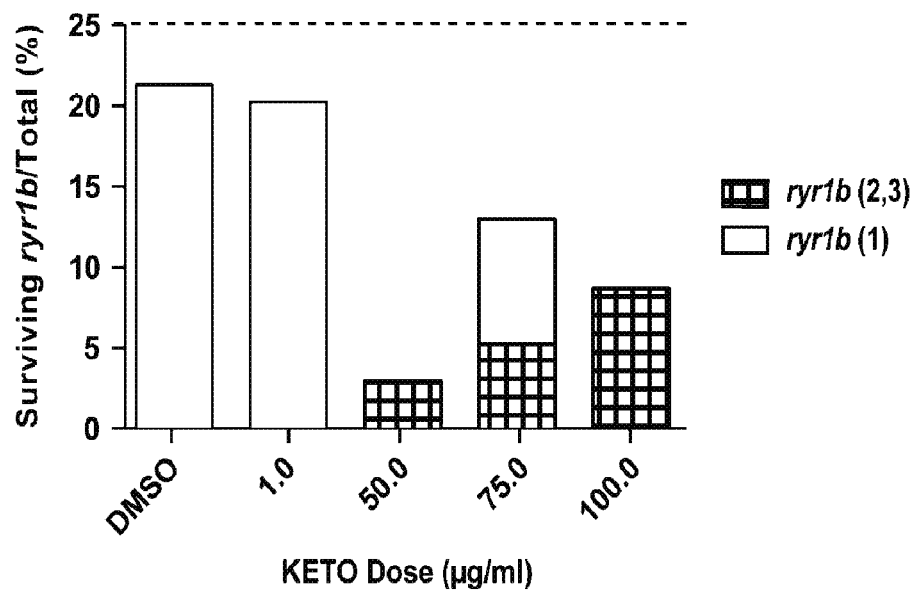
Figure 12C:
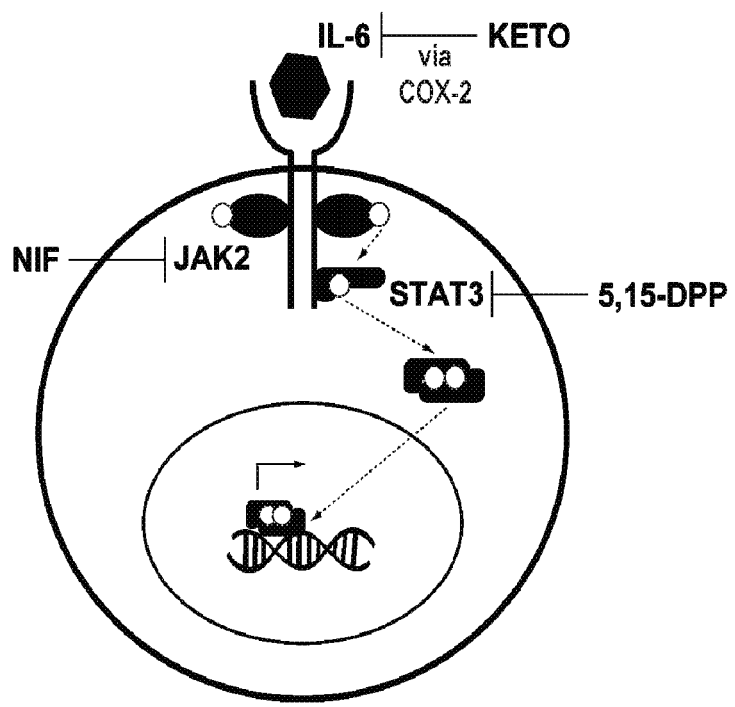

Example 6. Ketoprofen Candidate Further Supports a Role for JAK-STAT Signaling in Ryr1 Deficiency A second candidate compound, ketoprofen, is a nonsteroidal anti-inflammatory drug that reversibly inhibits cyclooxygenase-1 and -2 and reduces the production of pro-inflammatory prostaglandin precursors (FIG. 12A, top). A literature-based search revealed interleukin 6 (IL-6) to be one of the most prominently down-regulated precursors[46], and one that acts in the same molecular pathway as nifuroxazide (FIG. 12, bottom). Preliminary dose-response experiments have confirmed a relationship between ketoprofen and improvements in ryr1b mobility (FIG. 12B). It is believed that increased IL-6 production in Ryr1 deficiency leads to increases in JAK-STAT signaling downstream, and to changes in skeletal muscle gene expression that are not altered in healthy muscle (FIG. 12C)[17].

Discussion
Chemical Screening in the Ryr1b Zebrafish

Current research on congenital myopathies and muscular dystrophies is focused on using traditional methods to develop gene- and protein-based treatments[48-53]. These methods, while having great potential, are fraught with methodological and logistical problems that are general to the approach (i.e., delivery, immune rejection, carcinogenic potential, cost, etc.). The present ryr1b chemical screen represents a paradigm shift by taking a more pragmatic approach to drug development, by testing bioactive compounds in a validated vertebrate model and then using the identity of positive "hits" to learn more about the molecular pathways associated with core myopathies. The use of zebrafish to screen small molecule libraries was developed in collaboration with Boston Children's Hospital Division of Genetics and Genomics, and is innovative in its application to the ryr1b phenotype[37].

In contrast to target-based strategies, chemical screens in zebrafish are guided by a desired phenotype and allow for drug discovery without knowledge of specific molecular targets and mechanisms[38,54-57]. Embryonic and larval zebrafish are also permeable to small molecules and can be assayed in large numbers. Since zebrafish with homozygous recessive mutations in the ryr1b gene have been characterized as excellent models of core myopathy, the Prestwick2 library was screened for chemicals that could correct the severely impaired swimming behaviors of ryr1b mutants[30]. The two-tiered screening strategy of first pooling chemicals and then screening individual compounds resulted in the identification of twelve candidate compounds that decreased the number of phenotypically affected ryr1b larvae. Dose-response experiments are now in progress to identify those candidates that clearly demonstrate a causal relationship with improvements in the ryr1b phenotype.

JAK-STAT signaling and ROS in RyR1 Deficiency

Genetic- and pharmacological-based approaches have recently shown that increases in JAK-STAT signaling impair muscle regeneration by suppressing myogenic activities and satellite cell functions[42-44]. Follow-up studies conducted in vitro and in mice demonstrated that inhibition of either JAK kinase (using inhibitor AG490) or STAT3 (using inhibitor 5,15-DPP) promotes satellite cell expansion and rescues defects in muscle generation in both aging and dystrophic mouse models[43,44]. Intriguingly, nifuroxazide, a nitrofuran inhibitor of STAT3 transcription factor signaling, was one candidate compound found to rescue the muscle weakness of ryr1b larvae in a dose-dependent manner. Genotyping of the ryr1b gene in 5 dpf larvae treated with nifuroxazide (10 or 100 µg/mL) or with 5,15-DPP (100 µg/mL) beginning at 1 dpf revealed that ryr1b mutants were among larvae that exhibited wild-type touch-evoked escape behaviors. These data suggesting that STAT3 inhibition might prevent the onset of muscular abnormalities in zebrafish with ryr1b mutation, together with reports linking JAK-STAT signaling to myogenesis, prompted further studies of nifuroxazide in the model system.

Stat3 transcripts were significantly increased in ryr1b mutants relative to unaffected controls, while levels of Stat3 protein were similar between groups. However, phosphorylated Stat3 protein levels in ryr1b mutants treated with nifuroxazide at the lowest effective dose were largely reduced compared to ryr1b mutants treated with vehicle only. Such a decrease was not observed in between DMSO- and drug-treated unaffected control larvae. These observations indicate an increased sensitivity of Ryr1-deficient zebrafish to the inhibitor, and strongly suggest that JAK-STAT signaling is relevant to induction of the ryr1b phenotype. Although nifuroxazide did not dramatically impact ryr1b survival, chemical treatment definitively improved contractile strength, body morphology, and locomotive activities of mutants.

NADPH oxidase-generated reactive oxygen species (ROS) have been implicated in STAT3 activation[58]. Since Ryr1-deficient zebrafish demonstrate excessive production of ROS[31] as well as increased stat3 expression, it is quite plausible that there is a causal relationship between the two. Independent experiments showing that ryr1b swimming abnormalities can be treated with either N-acetylcysteine antioxidant[31] or JAK-STAT inhibitors serve as further support of this model. It is important to note that other candidates identified in our screen may also act within the same signaling pathway. Ketoprofen, a nonsteroidal anti-inflammatory drug that reversibly inhibits cyclooxygenase-1 and -2, inhibits the production of IL-6 in vitro and shows a dose-response relationship with ryr1b mutants[46]. Similarly, sulfasalazine is another anti-inflammatory candidate shown to inhibit IL-6 release in skeletal muscle[59]. IL-6 is a pleiotropic cytokine that exerts both pro-inflammatory and anti-inflammatory effects depending on the cellular context[60-62], and has been implicated in the pathogenesis of several neurodegenerative disorders, including Alzheimer's disease[63,64], Parkinson's disease[65], and multiple sclerosis[66]. IL-6 preferentially activates STAT3[67]. Activation of STAT3 also induces IL-6 mRNA production and increases secretion of IL-6 through the direct activation of IL-6 promoters[62]. Based on these reports, it is believed that ketoprofen (and potentially sulfasalazine) might act by decreasing JAK-STAT signaling in Ryr1-deficient zebrafish and restoring a feedback loop that becomes dysregulated under oxidizing conditions within their muscle cells.

Apart from candidates modulating JAK-STAT signaling, a fourth compound identified in the chemical screen has previously been reported to have beneficial effects on vertebrate models of muscle disease. Notably, the monoamine oxidase inhibitor pargyline hydrochloride significantly decreases myofiber apoptosis and increases muscle strength in mouse models of Duchenne and Ullrich congenital muscular dystrophies[68]. This study also found that ROS produced in mitochondria oxidize myofibrillar proteins important for contractile function in dystrophic muscle, such as tropomyosin, and pargyline hydrochloride corrects this defect at the molecular level.

The four candidates discussed herein validate the present screening strategy as a means to find pathways that might influence abnormalities within skeletal muscle, and also open up promising avenues for future studies with the ryr1b and sepn1 zebrafish.

REFERENCES FOR EXAMPLES

1. Fill, M. and Copello, J. A. (2002) Ryanodine receptor calcium release channels. *Physiol Rev,* 82, 893-922.
2. Lanner, J. T., Georgiou, D. K., Joshi, A. D. and Hamilton, S. L. (2010) Ryanodine receptors: structure, expression, molecular details, and function in calcium release. *Cold Spring Harb Perspect Biol,* 2, a003996.
3. Treves, S., Jungbluth, H., Muntoni, F. and Zorzato, F. (2008) Congenital muscle disorders with cores: the ryanodine receptor calcium channel paradigm. *Curr Opin Pharmacol,* 8, 319-326.
4. Valdivia, H. H. and Coronado, R. (1989) Inhibition of dihydropyridine-sensitive calcium channels by the plant alkaloid ryanodine. *FEBS Lett,* 244, 333-337.
5. MacLennan, D. H. and Phillips, M. S. (1992) Malignant hyperthermia. *Science,* 256, 789-794.
6. Robinson, R., Carpenter, D., Shaw, M. A., Halsall, J. and Hopkins, P. (2006) Mutations in RYR1 in malignant hyperthermia and central core disease. *Hum Mutat,* 27, 977-989.
7. Zhou, H., Lillis, S., Loy, R. E., Ghassemi, F., Rose, M. R., Norwood, F., Mills, K., Al-Sarraj, S., Lane, R. J., Feng, L. et al. (2010) Multi-minicore disease and atypical periodic paralysis associated with novel mutations in the skeletal muscle ryanodine receptor (RYR1) gene. *Neuromuscul Disord,* 20, 166-173.
8. Wilmshurst, J. M., Lillis, S., Zhou, H., Pillay, K., Henderson, H., Kress, W., Muller, C. R., Ndondo, A., Cloke, V., Cullup, T. et al. (2010) RYR1 mutations are a common cause of congenital myopathies with central nuclei. *Ann Neurol,* 68, 717-726.
9. Hernandez-Lain, A., Husson, I., Monnier, N., Farnoux, C., Brochier, G., Lacene, E., Beuvin, M., Viou, M., Manere, L., Claeys, K. G. et al. (2011) De novo RYR1 heterozygous mutation (I4898T) causing lethal core-rod myopathy in twins. *Eur J Med Genet,* 54, 29-33.
10. DeChene, E. T., Kang, P. B. and Beggs, A. H. (1993) Congenital fiber-type disproportion. In Pagon, R. A., Adam, M. P., Ardinger, H. H., Bird, T. D., Dolan, C. R., Fong, C. T., Smith, R. J. H. and Stephens, K. (eds.), In *GeneReviews®,* Seattle (Wash.).
11. Clarke, N. F., Waddell, L. B., Cooper, S. T., Perry, M., Smith, R. L., Kornberg, A. J., Muntoni, F., Lillis, S., Straub, V., Bushby, K. et al. (2010) Recessive mutations in RYR1 are a common cause of congenital fiber type disproportion. *Hum Mutat,* 31, E1544-1550.
12. Bharucha-Goebel, D. X., Santi, M., Medne, L., Zukosky, K., Dastgir, J., Shieh, P. B., Winder, T., Tennekoon, G., Finkel, R. S., Dowling, J. J. et al. (2013) Severe congenital RYR1-associated myopathy: the expanding clinicopathologic and genetic spectrum. *Neurology,* 80, 1584-1589.
13. Tong, J., Oyamada, H., Demaurex, N., Grinstein, S., McCarthy, T. V. and MacLennan, D. H. (1997) Caffeine and halothane sensitivity of intracellular Ca2+ release is altered by 15 calcium release channel (ryanodine receptor) mutations associated with malignant hyperthermia and/or central core disease. *J Biol Chem,* 272, 26332-26339.
14. Lynch, P. J., Tong, J., Lehane, M., Mallet, A., Giblin, L., Heffron, J. J., Vaughan, P., Zafra, G., MacLennan, D. H. and McCarthy, T. V. (1999) A mutation in the transmembrane/luminal domain of the ryanodine receptor is associated with abnormal Ca2+ release channel function and severe central core disease. *Proc Natl Acad Sci USA,* 96, 4164-4169.
15. Tong, J., McCarthy, T. V. and MacLennan, D. H. (1999) Measurement of resting cytosolic Ca2+ concentrations and Ca2+ store size in HEK-293 cells transfected with malignant hyperthermia or central core disease mutant Ca2+ release channels. *J Biol Chem,* 274, 693-702.
16. Avila, G., O'Brien, J. J. and Dirksen, R. T. (2001) Excitation—contraction uncoupling by a human central core disease mutation in the ryanodine receptor. *Proc Natl Acad Sci USA,* 98, 4215-4220.
17. Ducreux, S., Zorzato, F., Muller, C., Sewry, C., Muntoni, F., Quinlivan, R., Restagno, G., Girard, T. and Treves, S. (2004) Effect of ryanodine receptor mutations on interleukin-6 release and intracellular calcium homeostasis in human myotubes from malignant hyperthermia-susceptible individuals and patients affected by central core disease. *J Biol Chem,* 279, 43838-43846.
18. Avila, G. and Dirksen, R. T. (2001) Functional effects of central core disease mutations in the cytoplasmic region of the skeletal muscle ryanodine receptor. *J Gen Physiol,* 118, 277-290.
19. Zorzato, F., Yamaguchi, N., Xu, L., Meissner, G., Muller, C. R., Pouliquin, P., Muntoni, F., Sewry, C., Girard, T. and Treves, S. (2003) Clinical and functional effects of a deletion in a COOH-terminal lumenal loop of the skeletal muscle ryanodine receptor. *Hum Mol Genet,* 12, 379-388.
20. Dirksen, R. T. and Avila, G. (2004) Distinct effects on Ca2+ handling caused by malignant hyperthermia and central core disease mutations in RyR1. *Biophys J,* 87, 3193-3204.
21. Du, G. G., Khanna, V. K., Guo, X. and MacLennan, D. H. (2004) Central core disease mutations R4892W, I4897T and G4898E in the ryanodine receptor isoform 1 reduce the Ca2+ sensitivity and amplitude of Ca2+-dependent Ca2+ release. *Biochem J,* 382, 557-564.
22. Jungbluth, H., Sewry, C. A. and Muntoni, F. (2011) Core myopathies. *Semin Pediatr Neurol,* 18, 239-249.
23. Zhou, H., Rokach, O., Feng, L., Munteanu, I., Mamchaoui, K., Wilmshurst, J. M., Sewry, C., Manzur, A. Y., Pillay, K., Mouly, V. et al. (2013) RyR1 deficiency in congenital myopathies disrupts excitation-contraction coupling. *Hum Mutat,* 34, 986-996.
24. Treves, S., Vukcevic, M., Jeannet, P. Y., Levano, S., Girard, T., Urwyler, A., Fischer, D., Voit, T., Jungbluth, H., Lillis, S. et al. (2011) Enhanced excitation-coupled Ca(2+) entry induces nuclear translocation of NFAT and contributes to IL-6 release from myotubes from patients with central core disease. *Hum Mol Genet,* 20, 589-600.
25. Yang, T., Riehl, J., Esteve, E., Matthaei, K. I., Goth, S., Allen, P. D., Pessah, I. N. and Lopez, J. R. (2006) Pharmacologic and functional characterization of malignant hyperthermia in the R163C RyR1 knock-in mouse. *Anesthesiology,* 105, 1164-1175.
26. Chelu, M. G., Goonasekera, S. A., Durham, W. J., Tang, W., Lueck, J. D., Riehl, J., Pessah, I. N., Zhang, P., Bhattacharjee, M. B., Dirksen, R. T. et al. (2006) Heat- and anesthesia-induced malignant hyperthermia in an RyR1 knock-in mouse. *Faseb J,* 20, 329-330.
27. Durham, W. J., Aracena-Parks, P., Long, C., Rossi, A. E., Goonasekera, S. A., Boncompagni, S., Galvan, D. L., Gilman, C. P., Baker, M. R., Shirokova, N. et al. (2008) RyR1 S-nitrosylation underlies environmental heat stroke and sudden death in Y522S RyR1 knockin mice. *Cell,* 133, 53-65.
28. Zvaritch, E., Kraeva, N., Bombardier, E., McCloy, R. A., Depreux, F., Holmyard, D., Kraev, A., Seidman, C. E., Seidman, J. G., Tupling, A. R. et al. (2009) Ca2+ dysregulation in Ryr1(I4895T/wt) mice causes congenital myopathy with progressive formation of minicores, cores, and nemaline rods. *Proc Natl Acad Sci USA,* 106, 21813-21818.
29. Takeshima, H., Iino, M., Takekura, H., Nishi, M., Kuno, J., Minowa, O., Takano, H. and Noda, T. (1994) Excitation-contraction uncoupling and muscular degeneration in mice lacking functional skeletal muscle ryanodine-receptor gene. *Nature,* 369, 556-559.
30. Hirata, H., Watanabe, T., Hatakeyama, J., Sprague, S. M., Saint-Amant, L., Nagashima, A., Cui, W. W., Zhou, W. and Kuwada, J. Y. (2007) Zebrafish relatively relaxed mutants have a ryanodine receptor defect, show slow swimming and provide a model of multi-minicore disease. *Development,* 134, 2771-2781.
31. Dowling, J. J., Arbogast, S., Hur, J., Nelson, D. D., McEvoy, A., Waugh, T., Marty, I., Lunardi, J., Brooks, S. V., Kuwada, J. Y. et al. (2012) Oxidative stress and successful antioxidant treatment in models of RYR1-related myopathy. *Brain,* 135, 1115-1127.
32. Zhang, J. Z., Wu, Y., Williams, B. Y., Rodney, G., Mandel, F., Strasburg, G. M. and Hamilton, S. L. (1999) Oxidation of the skeletal muscle Ca2+ release channel alters calmodulin binding. *Am J Physiol,* 276, C46-53.
33. Aracena, P., Tang, W., Hamilton, S. L. and Hidalgo, C. (2005) Effects of S-glutathionylation and S-nitrosylation on calmodulin binding to triads and FKBP12 binding to type 1 calcium release channels. *Antioxid Redox Signal,* 7, 870-881.
34. Raturi, A., Ortiz-Sandoval, C. and Simmen, T. (2014) Redox dependence of endoplasmic reticulum (ER) Ca(2)(+) signaling. *Histol Histopathol,* 29, 543-552.
35. Westerfield, M. (2007) *The zebrafish book. A guide for the laboratory use of zebrafish (Danio rerio).* University of Oregon Press, Eugene.
36. Kimmel, C. B., Ballard, W. W., Kimmel, S. R., Ullmann, B. and Schilling, T. F. (1995) Stages of embryonic development of the zebrafish. *Dev Dyn,* 203, 253-310.
37. Kawahara, G., Karpf, J. A., Myers, J. A., Alexander, M. S., Guyon, J. R. and Kunkel, L. M. (2011) Drug screening in a zebrafish model of Duchenne muscular dystrophy. *Proc Natl Acad Sci USA,* 108, 5331-5336.
38. Zon, L. I. and Peterson, R. T. (2005) In vivo drug discovery in the zebrafish. *Nat Rev Drug Discov,* 4, 35-44.
39. Shen, X., Franzini-Armstrong, C., Lopez, J. R., Jones, L. R., Kobayashi, Y. M., Wang, Y., Kerrick, W. G., Caswell, A. H., Potter, J. D., Miller, T. et al. (2007) Triadins modulate intracellular Ca(2+) homeostasis but are not essential for excitation-contraction coupling in skeletal muscle. *J Biol Chem,* 282, 37864-37874.
40. Nelson, E. A., Walker, S. R., Kepich, A., Gashin, L. B., Hideshima, T., Ikeda, H., Chauhan, D., Anderson, K. C. and Frank, D. A. (2008) Nifuroxazide inhibits survival of multiple myeloma cells by directly inhibiting STAT3. *Blood,* 112, 5095-5102.
41. Uehara, Y., Mochizuki, M., Matsuno, K., Haino, T. and Asai, A. (2009) Novel high-throughput screening system for identifying STAT3-SH2 antagonists. *Biochem Biophys Res Commun,* 380, 627-631.
42. Jang, Y. N. and Baik, E. J. (2013) JAK-STAT pathway and myogenic differentiation. *Jakstat,* 2, e23282.
43. Tierney, M. T., Aydogdu, T., Sala, D., Malecova, B., Gatto, S., Puri, P. L., Latella, L. and Sacco, A. (2014) STAT3 signaling controls satellite cell expansion and skeletal muscle repair. *Nat Med,* 20, 1182-1186.
44. Price, F. D., von Maltzahn, J., Bentzinger, C. F., Dumont, N. A., Yin, H., Chang, N.C., Wilson, D. H., Frenette, J. and Rudnicki, M. A. (2014) Inhibition of JAK-STAT signaling stimulates adult satellite cell function. *Nat Med,* 20, 1174-1181.
45. Franzini-Armstrong, C. and Protasi, F. (1997) Ryanodine receptors of striated muscles: a complex channel capable of multiple interactions. *Physiol Rev,* 77, 699-729.
46. Tsuboi, I., Tanaka, H., Nakao, M., Shichijo, S. and Itoh, K. (1995) Nonsteroidal anti-inflammatory drugs differentially regulate cytokine production in human lymphocytes: up-regulation of TNF, IFN-gamma and IL-2, in contrast to down-regulation of IL-6 production. *Cytokine,* 7, 372-379.
47. Rawlings, J. S., Rosler, K. M. and Harrison, D. A. (2004) The JAK/STAT signaling pathway. *J Cell Sci,* 117, 1281-1283.
48. Wu, Z., Asokan, A. and Samulski, R. J. (2006) Adeno-associated virus serotypes: vector toolkit for human gene therapy. *Mol Ther,* 14, 316-327.
49. Buj-Bello, A., Fougerousse, F., Schwab, Y., Messaddeq, N., Spehner, D., Pierson, C. R., Durand, M., Kretz, C., Danos, O., Douar, A. M. et al. (2008) AAV-mediated intramuscular delivery of myotubularin corrects the myotubular myopathy phenotype in targeted murine muscle and suggests a function in plasma membrane homeostasis. *Hum Mol Genet,* 17, 2132-2143.
50. Lawlor, M. W., Read, B. P., Edelstein, R., Yang, N., Pierson, C. R., Stein, M. J., Wermer-Colan, A., Buj-Bello, A., Lachey, J. L., Seehra, J. S. et al. (2011) Inhibition of activin receptor type IIB increases strength and lifespan in myotubularin-deficient mice. *Am J Pathol,* 178, 784-793.
51. Lawlor, M. W., Armstrong, D., Viola, M. G., Widrick, J. J., Meng, H., Grange, R. W., Childers, M. K., Hsu, C. P., O'Callaghan, M., Pierson, C. R. et al. (2013) Enzyme replacement therapy rescues weakness and improves muscle pathology in mice with X-linked myotubular myopathy. *Hum Mol Genet*, 22, 1525-1538.
52. Childers, M. K., Joubert, R., Poulard, K., Moal, C., Grange, R. W., Doering, J. A., Lawlor, M. W., Rider, B. E., Jamet, T., Daniele, N. et al. (2014) Gene therapy prolongs survival and restores function in murine and canine models of myotubular myopathy. *Sci Transl Med*, 6, 220ra210.
53. Braun, R., Wang, Z., Mack, D. L. and Childers, M. K. (2014) Gene therapy for inherited muscle diseases: where genetics meets rehabilitation medicine. *Am J Phys Med Rehabil*, 93, S97-107.
54. Dooley, K. and Zon, L. I. (2000) Zebrafish: a model system for the study of human disease. *Curr Opin Genet Dev*, 10, 252-256.
55. Peterson, R. T., Link, B. A., Dowling, J. E. and Schreiber, S. L. (2000) Small molecule developmental screens reveal the logic and timing of vertebrate development. *Proc Natl Acad Sci USA*, 97, 12965-12969.
56. Pichler, F. B., Laurenson, S., Williams, L. C., Dodd, A., Copp, B. R. and Love, D. R. (2003) Chemical discovery and global gene expression analysis in zebrafish. *Nature Biotechnol*, 21, 879-883.
57. Stern, H. M., Murphey, R. D., Shepard, J. L., Amatruda, J. F., Straub, C. T., Pfaff, K. L., Weber, G., Tallarico, J. A., King, R. W. and Zon, L. I. (2005) Small molecules that delay S phase suppress a zebrafish bmyb mutant. *Nature Chem Biol*, 1, 366-370.
58. Yoon, S., Woo, S. U., Kang, J. H., Kim, K., Kwon, M. H., Park, S., Shin, H. J., Gwak, H. S. and Chwae, Y. J. (2010) STAT3 transcriptional factor activated by reactive oxygen species induces IL6 in starvation-induced autophagy of cancer cells. *Autophagy*, 6, 1125-1138.
59. Lappas, M., Yee, K., Permezel, M. and Rice, G. E. (2005) Sulfasalazine and BAY 11-7082 interfere with the nuclear factor-kappa B and I kappa B kinase pathway to regulate the release of proinflammatory cytokines from human adipose tissue and skeletal muscle in vitro. *Endocrinology*, 146, 1491-1497.
60. Kishimoto, T., Akira, S. and Taga, T. (1992) Interleukin-6 and its receptor: a paradigm for cytokines. *Science*, 258, 593-597.
61. Jones, S. A., Horiuchi, S., Topley, N., Yamamoto, N. and Fuller, G. M. (2001) The soluble interleukin 6 receptor: mechanisms of production and implications in disease. *Faseb J*, 15, 43-58.
62. Babon, J. J., Varghese, L. N. and Nicola, N. A. (2014) Inhibition of IL-6 family cytokines by SOCS3. *Semin Immunol*, 26, 13-19.
63. Bauer, J., Strauss, S., Volk, B. and Berger, M. (1991) IL-6-mediated events in Alzheimer's disease pathology. *Immunol Today*, 12, 422.
64. Campbell, I. L., Abraham, C. R., Masliah, E., Kemper, P., Inglis, J. D., Oldstone, M. B. and Mucke, L. (1993) Neurologic disease induced in transgenic mice by cerebral overexpression of interleukin 6. *Proc Natl Acad Sci USA*, 90, 10061-10065.
65. Blum-Degen, D., Muller, T., Kuhn, W., Gerlach, M., Przuntek, H. and Riederer, P. (1995) Interleukin-1 beta and interleukin-6 are elevated in the cerebrospinal fluid of Alzheimer's and de novo Parkinson's disease patients. *Neurosci Lett*, 202, 17-20.
66. Frei, K., Fredrikson, S., Fontana, A. and Link, H. (1991) Interleukin-6 is elevated in plasma in multiple sclerosis. *J Neuroimmunol*, 31, 147-153.
67. Sengupta, T. K., Schmitt, E. M. and Ivashkiv, L. B. (1996) Inhibition of cytokines and JAK-STAT activation by distinct signaling pathways. *Proc Natl Acad Sci USA*, 93, 9499-9504.
68. Menazza, S., Blaauw, B., Tiepolo, T., Toniolo, L., Braghetta, P., Spolaore, B., Reggiani, C., Di Lisa, F., Bonaldo, P. and Canton, M. (2010) Oxidative stress by monoamine oxidases is causally involved in myofiber damage in muscular dystrophy. *Hum Mol Genet*, 19, 4207-4215.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of treating a ryanodine receptor 1(RyR1)-related myopathy, the method comprising:
    administering to a subject having a RyR1-related myopathy an effective amount of an inhibitor of Janus kinase-Signal Transducer and Activator of Transcription (JAK-STAT) pathway.

2. The method of claim 1, wherein the inhibitor of JAK-STAT is a small molecule, wherein the small molecule is an organic compound having a molecular weight of less than 900 daltons.

3. The method of claim 1, wherein the inhibitor of JAK-STAT is an antisense oligonucleotide.

4. The method of claim 1, wherein the inhibitor of JAK-STAT is a small interfering RNA (siRNA).

5. The method of claim 1, wherein the inhibitor of JAK-STAT is nifuroxazide.

6. The method of claim 1, wherein the inhibitor of JAK-STAT is ketoprofen.

7. The method of claim 1, wherein the inhibitor of JAK-STAT is sulfasalazine.

8. The method of claim 1, wherein the inhibitor of JAK-STAT is 5,15-diphenylporphyrin.

9. The method of claim 1, wherein the inhibitor of JAK-STAT is AG490.

10. The method of claim 1, wherein the inhibitor of JAK-STAT is an inhibitor of JAK.

11. The method of claim 1, wherein the inhibitor of JAK-STAT is an inhibitor of STAT.

12. The method of claim 1, wherein the inhibitor of JAK-STAT is an inhibitor of STAT3.

13. The method of claim 1, wherein the RYR1-related myopathy is selected from the group consisting of: central core disease (CCD), multiminicore disease (MmD), centronuclear myopathy (CNM), nemaline myopathy (NM), core-rod myopathy, and congenital fiber-type disproportion (CFTD).

* * * * *